(12) United States Patent
Kosuge et al.

(10) Patent No.: US 8,084,937 B2
(45) Date of Patent: Dec. 27, 2011

(54) BINAPHTHYL COMPOUND AND ORGANIC LIGHT EMITTING ELEMENT USING THE SAME

(75) Inventors: Tetsuya Kosuge, Kawasaki (JP); Jun Kamatani, Tokyo (JP); Shigemoto Abe, Tokyo (JP); Ryota Ooishi, Yokohama (JP); Kengo Kishino, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 395 days.

(21) Appl. No.: 12/244,567

(22) Filed: Oct. 2, 2008

(65) Prior Publication Data

US 2009/0091252 A1    Apr. 9, 2009

(30) Foreign Application Priority Data

Oct. 3, 2007    (JP) ................. 2007-259866

(51) Int. Cl.
*H01J 1/63*     (2006.01)
*C07C 23/18*    (2006.01)
*C07C 43/205*   (2006.01)
*C07D 211/54*   (2006.01)
*C07D 471/04*   (2006.01)

(52) U.S. Cl. ............ 313/504; 585/26; 585/27; 428/690; 428/917; 313/506; 546/85; 546/122; 546/152

(58) Field of Classification Search .................. None
See application file for complete search history.

(56) References Cited

U.S. PATENT DOCUMENTS 7,316,851 B2 *    1/2008    Kita et al. ................. 428/690
(Continued)

FOREIGN PATENT DOCUMENTS

| JP | 2003-081923 | 3/2003 |
|----|-------------|--------|
| JP | 2004-018510 | 1/2004 |
| JP | 2004-043349 | 2/2004 |

(Continued)

OTHER PUBLICATIONS

Search Report dated Feb. 17, 2009 for EP 08165687.8-1211.

*Primary Examiner* — Jennifer Chriss
*Assistant Examiner* — Camie Thompson
(74) *Attorney, Agent, or Firm* — Fitzpatrick, Cella, Harper & Scinto

(57) ABSTRACT

The present invention provides a novel binaphthyl compound and an organic light emitting element having a good light emitting efficiency and a high durability at a low driving voltage. An organic light emitting element including an anode and a cathode, and a layer including an organic compound sandwiched between the anode and the cathode, wherein one of the anode and the cathode is transparent or semi-transparent, and the layer including an organic compound includes at least one binaphthyl compound represented by the following general formula [I]:

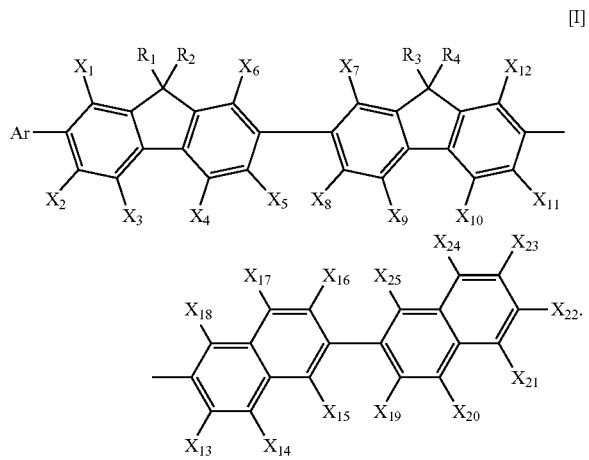

10 Claims, 5 Drawing Sheets

U.S. PATENT DOCUMENTS

| | | | |
|---|---|---|---|
| 2004/0106003 A1* | 6/2004 | Chen et al. | 428/690 |
| 2005/0095456 A1 | 5/2005 | Takeda | 428/690 |
| 2005/0175857 A1 | 8/2005 | Coggan et al. | 428/690 |
| 2006/0093857 A1 | 5/2006 | Nakashima et al. | 428/690 |
| 2006/0159956 A1 | 7/2006 | Ito et al. | 428/690 |
| 2007/0013294 A1* | 1/2007 | Jen et al. | 313/504 |
| 2007/0088185 A1 | 4/2007 | Kubota et al. | 585/407 |
| 2007/0205715 A1 | 9/2007 | Saitoh et al. | 313/504 |
| 2009/0066227 A1 | 3/2009 | Okinaka et al. | 313/504 |

FOREIGN PATENT DOCUMENTS

| | | |
|---|---|---|
| JP | 2005-019219 | 1/2005 |
| JP | 2005-222948 | 8/2005 |
| JP | 2006-151966 | 6/2006 |
| WO | WO 2005/123634 A1 | 12/2005 |
| WO | WO 2006/104044 A1 | 10/2006 |
| WO | WO 2007/046658 A1 | 4/2007 |
| WO | WO 2007/072741 | 6/2007 |

* cited by examiner

EXAMPLE COMPOUND A-02

EXAMPLE COMPOUND B-18

BINAPHTHYL COMPOUND AND ORGANIC LIGHT EMITTING ELEMENT USING THE SAME

BACKGROUND OF THE INVENTION

1. Field of the Invention

The present invention relates to a binaphthyl compound and an organic light emitting element using the same.

2. Description of the Related Art

The organic light emitting element is an element having a thin film which contains a fluorescence emitting organic compound or a phosphorescence emitting organic compound sandwiched between an anode and a cathode. Electrons and holes (positive holes) are injected from the respective electrodes to generate excitons of the fluorescence emitting organic compound or the phosphorescence emitting organic compound, and the organic light emitting element emits light when these excitons come back to the ground state.

Recent progress in the organic light emitting element is remarkable, which includes high brightness at a low applied voltage, diversification of the wavelength of the emitted light, high-speed response, and reduction in thickness and weight of the light emitting device. From this, the organic light emitting element suggests possibility to broader use.

However, optical power with further higher brightness or higher conversion efficiency is necessary under the present conditions. In addition, there are still many problems in the aspect of durability such as deterioration with time by long time use and deterioration by atmospheric gas containing oxygen and/or moisture. Furthermore, when application to full color displays is considered, emission of blue, green and red lights with high color purity is needed, but it cannot be said that such problems have been fully solved.

In consideration of these problems, there have been conducted a number of studies on aromatic compounds and condensed polycyclic aromatic compounds usable as light-emitting organic compounds which constitute the emitting light layer and the like. It is hard to say, however, that compounds having fully satisfactory emitting light brightness and durability have been obtained.

In the meantime, Japanese Patent Application Laid-Open No. 2004-018510, Japanese Patent Application Laid-Open No. 2004-043349, Japanese Patent Application Laid-Open No. 2005-019219, Japanese Patent Application Laid-Open No. 2005-222948 (corresponding to US 2005/0175857), WO 2005/123634 pamphlet, Japanese Patent Application Laid-Open No. 2006-151966 (corresponding to US 2006/0093857), WO 2006/104044 pamphlet and WO 2007/046658 pamphlet can be mentioned as those exemplifying specific examples of aromatic compounds and condensed polycyclic aromatic compounds usable as light-emitting organic compounds which constitute the light emitting layer and the like.

SUMMARY OF THE INVENTION

An object of the present invention is to provide a novel binaphthyl compound. Another object of the present invention is to provide an organic light emitting element having good light emitting efficiency and high durability at a low driving voltage.

The binaphthyl compound of the present invention is represented by the following general formula [I]:

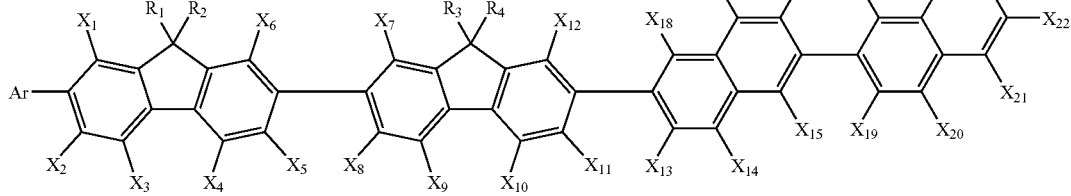

(In Formula [I], Ar represents a hydrogen atom or a substituent group selected from the group consisting of a substituted or unsubstituted alkyl group, a substituted or unsubstituted alkoxy group, a substituted or unsubstituted phenyl group, a substituted or unsubstituted fluorenyl group and a substituted or unsubstituted heteroaromatic ring group; $X_1$ to $X_{25}$ each represents a hydrogen atom, a substituent group selected from the group consisting of a substituted or unsubstituted alkyl group and a substituted or unsubstituted alkoxy group; and $R_1$ to $R_4$ each represents a hydrogen atom or a substituted or unsubstituted alkyl group).

According to the present invention, an organic light emitting element having good light emitting efficiency and high driving durability at a low driving voltage can be provided.

Further features of the present invention will become apparent from the following description of exemplary embodiments with reference to the attached drawings.

DESCRIPTION OF THE EMBODIMENTS

Figure 1:
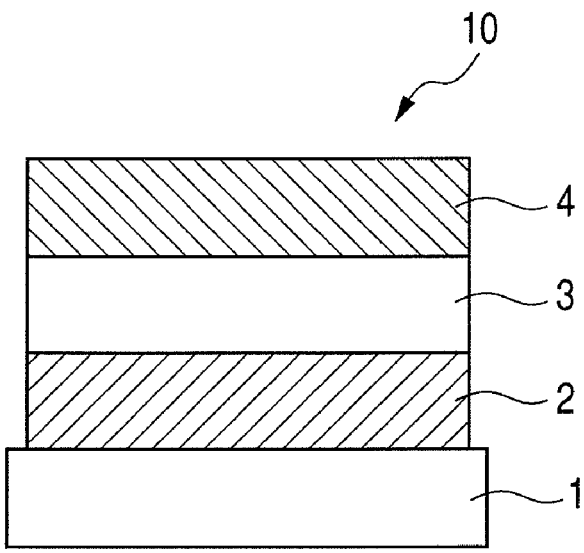
FIG. 1 is a cross-sectional view illustrating a first embodiment in the organic light emitting element of the present invention.

Hereinbelow, the present invention is described in detail. First, the binaphthyl compound of the present invention is described.

The binaphthyl compound of the present invention is represented by the following general formula [I].

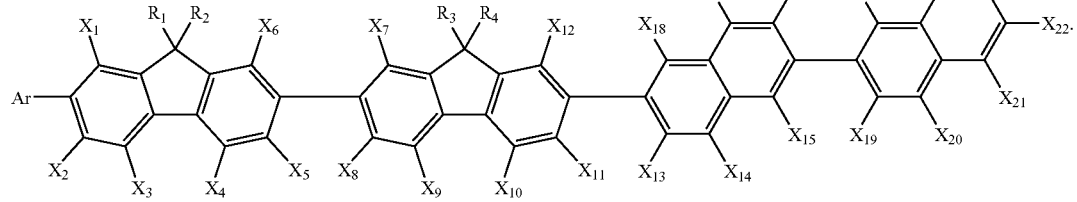

In Formula [I], Ar represents a hydrogen atom or a substituent group selected from the group consisting of a substituted or unsubstituted alkyl group, a substituted or unsubstituted alkoxy group, a substituted or unsubstituted phenyl group, a substituted or unsubstituted fluorenyl group and a substituted or unsubstituted heteroaromatic ring group.

Specific examples of the alkyl group represented by Ar include a methyl group, an ethyl group, an n-propyl group, an iso-propyl group, an n-butyl group, an iso-butyl group, a sec-butyl group, a tert-butyl group, an n-pentyl group, a neo-pentyl group, an n-hexyl group, an n-octyl group, an n-decyl, an n-dodecyl, a cyclopropyl group, a cyclobutyl group, a cyclopentyl group, a cyclohexyl group, a norbornyl group and an adamantyl group but, needless to say, it is not limited to these.

Specific examples of the alkoxy group represented by Ar include a methoxy group, an ethoxy group, an iso-propoxy group, a tert-butoxy group, an allyloxy group and a benzyloxy group but, needless to say, it is not limited to these.

Specific examples of the heteroaromatic ring group represented by Ar include a pyridyl group, a pyridazyl group, a pyrimidinyl group, a pyrazinyl group, a triazyl group, a quinolyl group, an isoquinolyl group, a phthalazinyl group, a quinazolinyl group, a quinoxalinyl group, a naphthylizinyl group, an acridinyl group, a benzoquinolyl group, a phenanthrolyl group, a monoazafluorenyl group, a diazafluorenyl group, a phenazinyl group, a pyrrolyl group, a pyrazolyl group, an imidazolyl group, a triazolyl group, an indolyl group, an indolizinyl group, a benzimidazolyl group, a carbazolyl group, a benzocarbazolyl group, a thienyl group, a benzothienyl group, a dibenzothienyl group, a furyl group, a benzofuryl group, an isobenzofuryl group, a dibenzofuryl group, an oxazolyl group, an isoxazolyl group, a benzoxazolyl group, an oxadiazolyl group, a thiazolyl group, an isothiazolyl group, a benzothiazolyl group, a thiadiazolyl group but, needless to say, it is not limited to these.

Examples of the substituent group which the alkyl group, alkoxy group, phenyl group, fluorenyl group and heteroaromatic ring group mentioned above may further have include an alkyl group such as a methyl group, a trifluoromethyl group, an ethyl group, a propyl group, an iso-butyl group and a tert-butyl group; an aromatic ring group such as a phenyl group, a tert-butylphenyl group, a dimethylphenyl group, a naphthyl group, a phenanthryl group, a fluorenyl group, a 9,9-dimethylfluorenyl group, a 9,9-diethylfluorenyl group, a 9,9-di-(n-hexyl)fluorenyl group, a bis-(9,9-diethylfluorenyl) group and substituent groups represented below

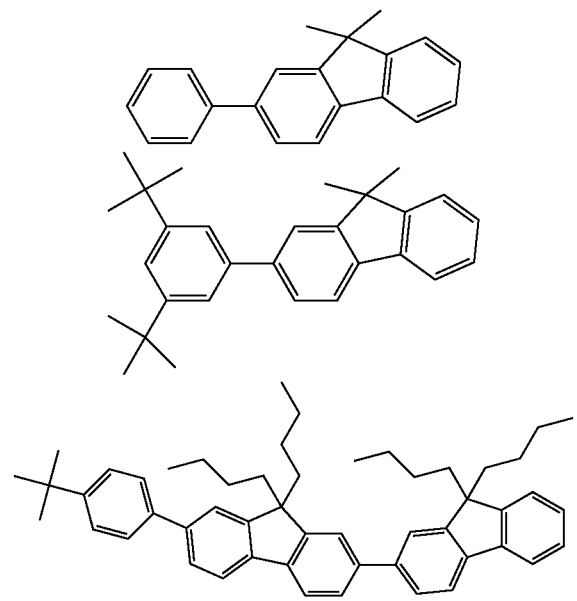

a heteroaromatic ring group such as a thienyl group, a pyrrolyl group and a pyridyl group; a substituted amino group such as a dimethylamino group, a diethylamino group, a dibenzylamino group, a diphenylamino group, a ditolylamino group, a dianisolylamino group and a naphthylphenylamino group; an alkoxy group such as a methoxy group and an ethoxy group; an aryloxy group such as a phenoxy group and a naphthoxy group; a halogen atom such as fluorine, chlorine, bromine and iodine; a hydroxyl group, a cyano group and a nitro group but, needless to say, it is not limited to these.

In Formula [I], $X_1$ to $X_{25}$ each represents a hydrogen atom or a substituent group selected from the group consisting of a substituted or unsubstituted alkyl group and a substituted or unsubstituted alkoxy group.

Specific examples of the alkyl group represented by $X_1$ to $X_{25}$ include a methyl group, an ethyl group, an n-propyl group, an iso-propyl group, an n-butyl group, an iso-butyl group, a sec-butyl group, a tert-butyl group, an n-pentyl group, a neopentyl group, an n-hexyl group, an n-octyl group, an n-decyl group, an n-dodecyl group, a cyclopropyl group, a cyclobutyl group, a cyclopentyl group, a cyclohexyl group, a norbornyl group and an adamantyl group but, needless to say, it is not limited to these.

Specific examples of the alkoxy group represented by $X_1$ to $X_{25}$ include a methoxy group, an ethoxy group, an iso-propoxy group, a tert-butoxy group, an allyloxy group and a benzyloxy group but, needless to say, it is not limited to these.

Examples of the substituent group which the alkyl group and alkoxy group mentioned above may further have include an alkyl group such as a methyl group, an ethyl group and a propyl group; a hydrocarbon aromatic ring group such as a phenyl group, a phenanthryl group and a fluorenyl group; a heteroaromatic ring group such as a thienyl group, a pyrrolyl group and a pyridyl group; a substituted amino group such as a dimethylamino group, a diethylamino group, a dibenzylamino group, a diphenylamino group, a ditolylamino group and a dianisolylamino group; an alkoxy group such as a methoxy group and an ethoxy group; an aryloxy group such as a phenoxy group and a naphthoxy group; a halogen atom such as fluorine, chlorine, bromine and iodine; a hydroxyl group, a cyano group and a nitro group but, needless to say, it is not limited to these.

In Formula [I], $R_1$ to $R_4$ each represents a hydrogen atom or a substituted or unsubstituted alkyl group.

Specific examples of the alkyl group represented by $R_1$ to $R_4$ include a methyl group, an ethyl group, an n-propyl group, an iso-propyl group, an n-butyl group, an iso-butyl group, a sec-butyl group, a tert-butyl group, an n-pentyl group, a neopentyl group, an n-hexyl group, an n-octyl group, an n-decyl, an n-dodecyl, a cyclopropyl group, a cyclobutyl group, a cyclopentyl group, a cyclohexyl group, a norbornyl group and an adamantyl group but, needless to say, it is not limited to these.

Examples of the substituent group which the alkyl group mentioned above may further have include an alkyl group such as a methyl group, an ethyl group and a propyl group; a hydrocarbon aromatic ring group such as a phenyl group, a phenanthryl group and a fluorenyl group; a heteroaromatic ring group such as a thienyl group, a pyrrolyl group and a pyridyl group; a substituted amino group such as a dimethylamino group, a diethylamino group, a dibenzylamino group, a diphenylamino group, a ditolylamino group and a dianisolylamino group; an alkoxy group such as a methoxy group and an ethoxy group; an aryloxy group such as a phenoxy group and a naphthoxy group; a halogen atom such as fluorine, chlorine, bromine and iodine; a hydroxyl group, a cyano group and a nitro group but, needless to say, it is not limited to these.

In addition, all or part of the hydrogen atoms present in the main skeleton or a substituent group may be substituted with heavy hydrogen in the binaphthyl compound of Formula [I].

The binaphthyl compound of Formula [I] is preferably a compound represented by Formula [II].

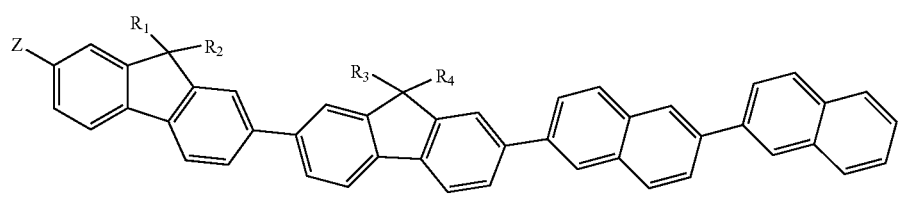

(II)

In Formula [II], $R_1$ to $R_4$ are the same as $R_1$ to $R_4$ in Formula [I].

In Formula [II], Z represents a hydrogen atom or a substituted or unsubstituted fluorenyl group.

The substituent group which the fluorenyl group represented by Z may further have is the same as the substituent group which, when Ar of Formula [I] is a fluorenyl group, the fluorenyl group may further have.

Next, synthesis method of the binaphthyl compound of the present invention is described.

The binaphthyl compound of the present invention can be synthesized by Suzuki-Miyaura coupling reaction represented by the following Formulas [III] and [IV] which uses a boronate compound, a halogenated compound and a tetrakis(triphenylphosphine)palladium catalyst.

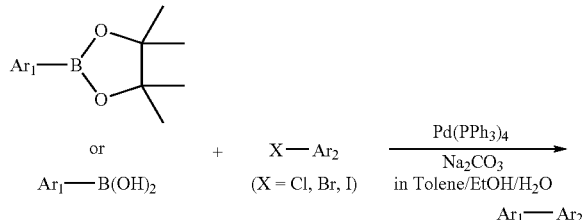

[III]

(In the formula, $Ar_1$ and $Ar_2$ each represents an aromatic ring group or a heteroaromatic ring group; and X represents a chlorine, bromine or iodine atom.)

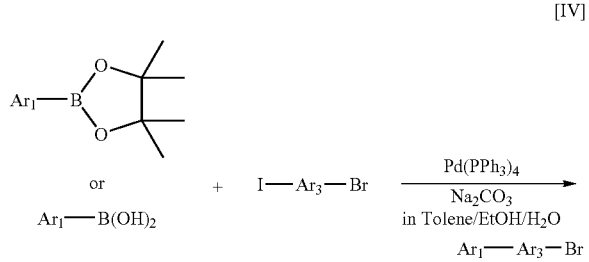

[IV]

(In the formula, Ar$_3$ represents a hydrocarbon aromatic ring group.)

The boronate compound used in the reaction of Formulas [III] and [IV] can be obtained from a halogenated precursor by the reaction represented by the following Formula [V].

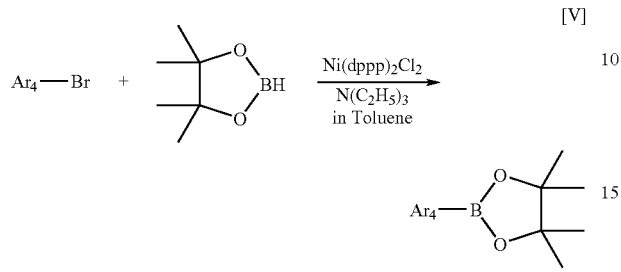

(In the formula, Ar$_4$ represents an aromatic ring group.)

Here, when the reaction is performed at a 1:1 equivalent ratio of the boronate compound and the iodobromo compound in the reaction of Formula [IV], iodine is selectively reacted to efficiently produce a monobromo compound. Then, this monobromo compound is used in the reaction of Formula [III] as it is or this compound is converted to a boronate ester by the reaction of Formula [V] and then used in the reaction of Formula [IV]. The binaphthyl compound of the present invention having a desired aromatic ring linked can be synthesized by adopting these steps.

Among halogenated compounds, boronate compounds and iodobromo compounds usable in the synthesis of the binaphthyl compound of the present invention, representative compounds are shown below but, needless to say, the present invention is not limited to these.

[Halogenated Compounds]

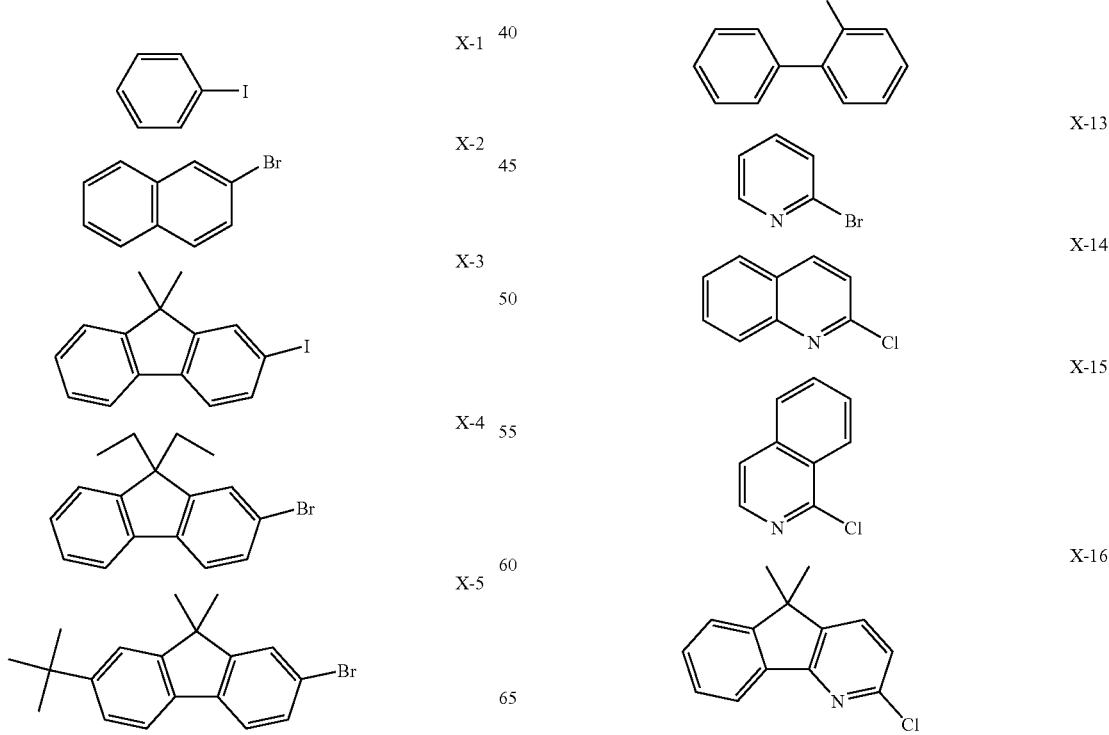

-continued

X-17

X-18

X-19

X-20

X-21

X-22

X-23

X-24

X-25

X-26

-continued

X-27

X-28

X-29

X-30

X-31

X-32

X-33

X-34

X-35

[Boronate Compounds]

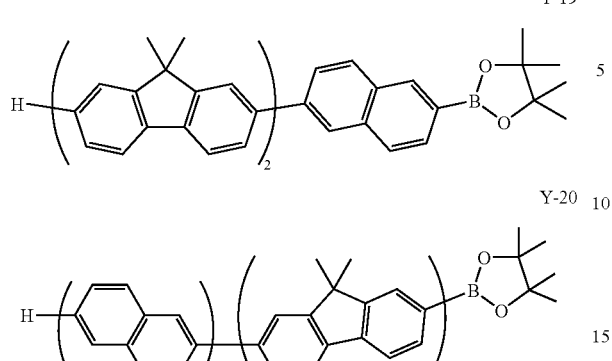

[Iodobromo Compounds]

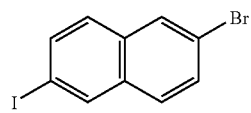

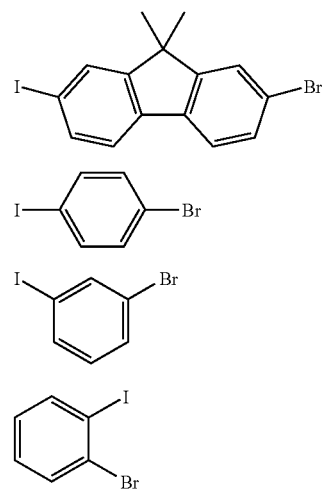

The binaphthyl compound of the present invention can be synthesized by performing the reactions of Formula [III] to Formula [V] using the compounds shown above.

The specific structures of the binaphthyl compound for organic light emitting elements of the present invention are shown below but, needless to say, the present invention is not limited to these.

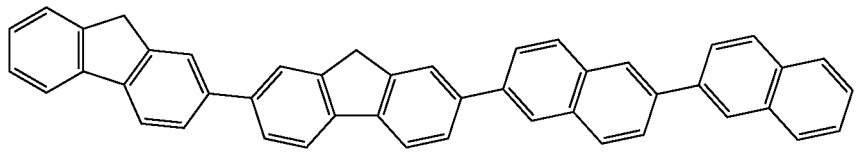

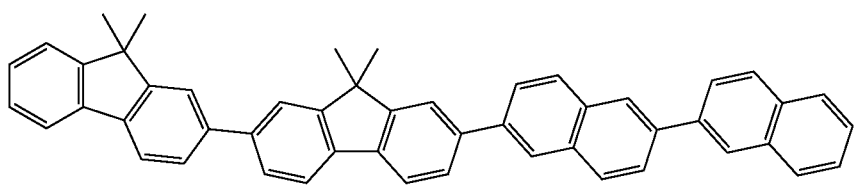

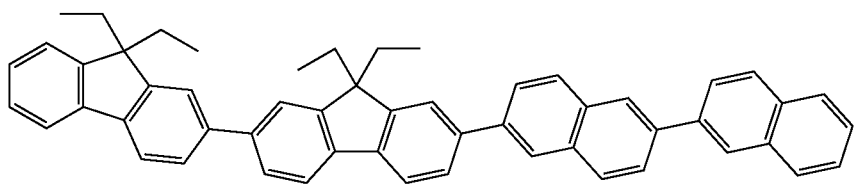

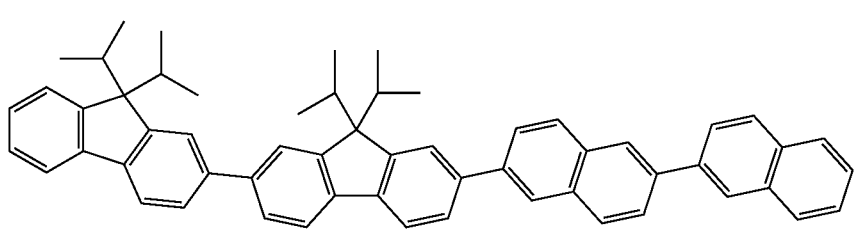

-continued
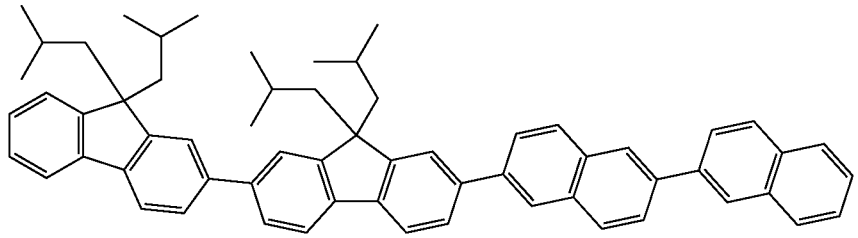
A-05
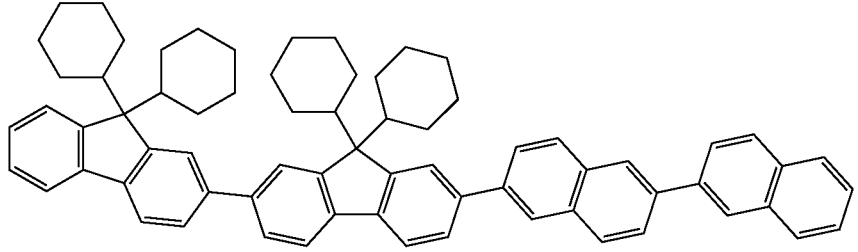
A-06
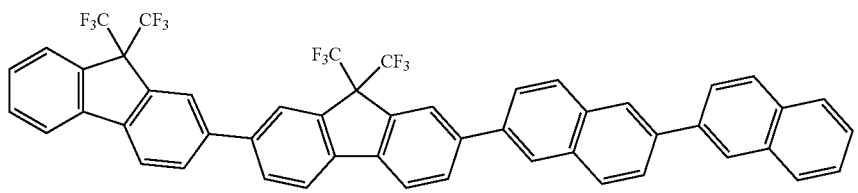
A-07
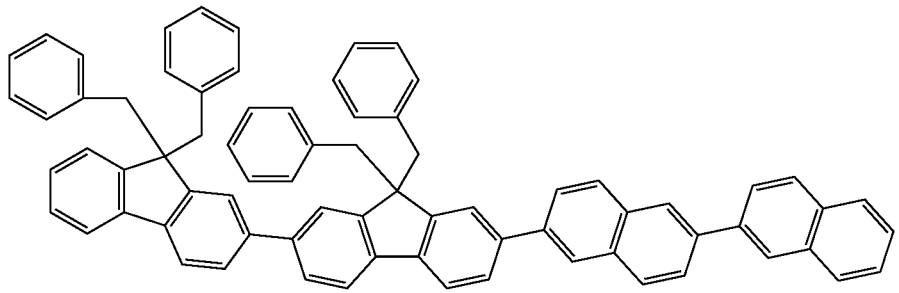
A-08
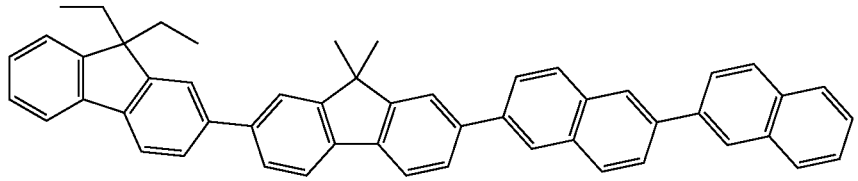
A-09
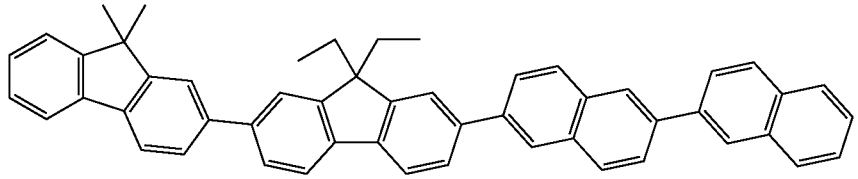
A-10
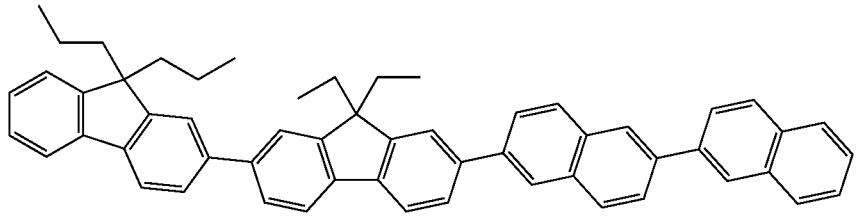
A-11

-continued
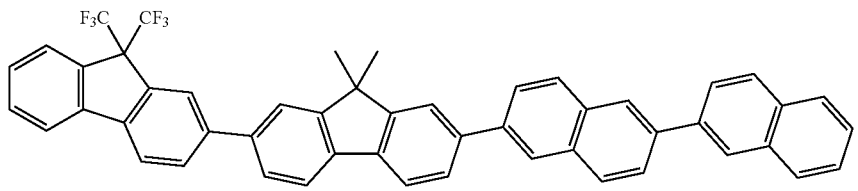
A-12
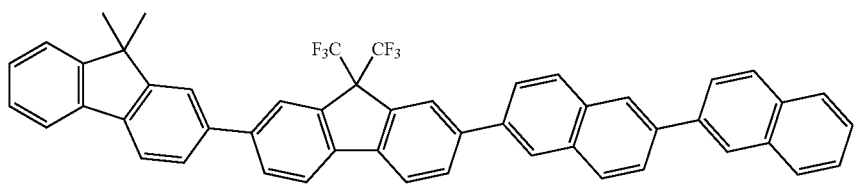
A-13
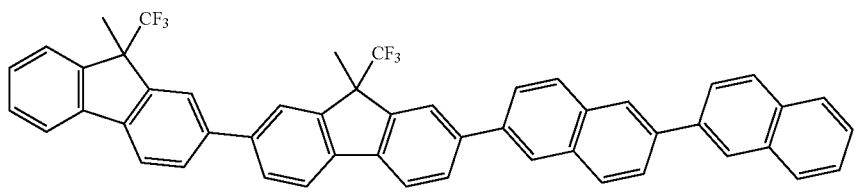
A-14
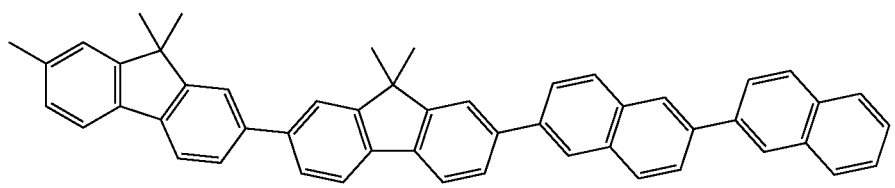
A-15
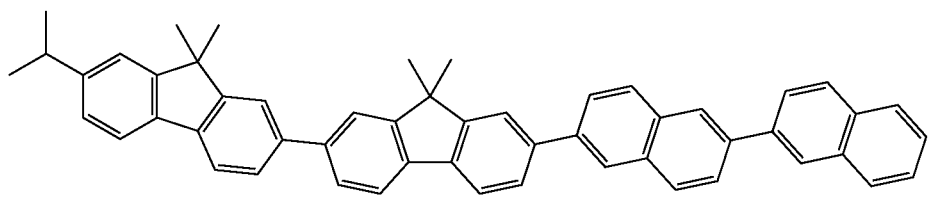
A-16
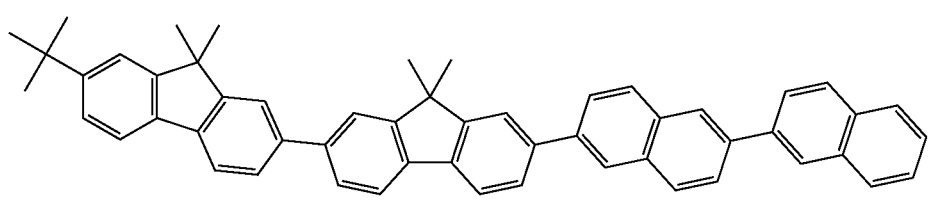
A-17
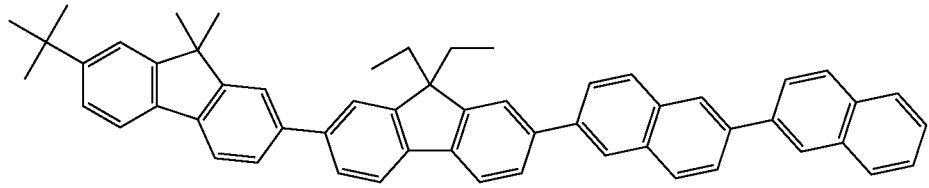
A-18
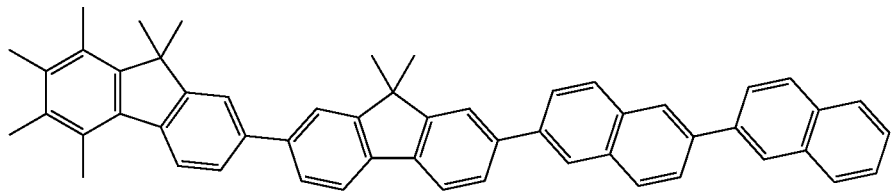
A-19

-continued
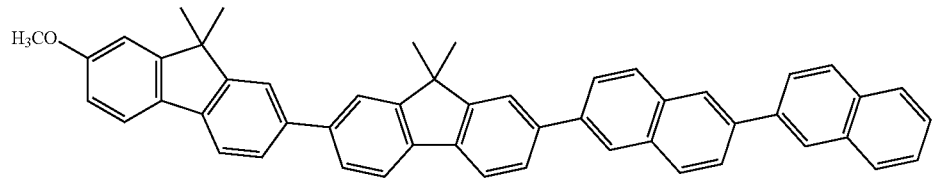
A-20
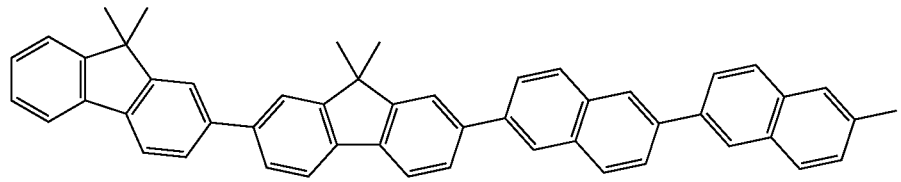
A-21
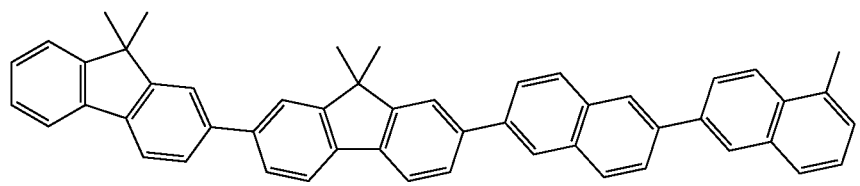
A-22
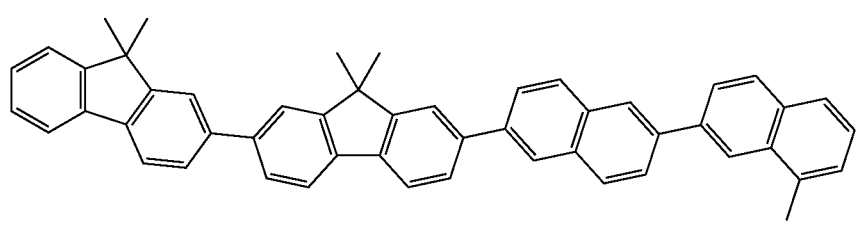
A-23
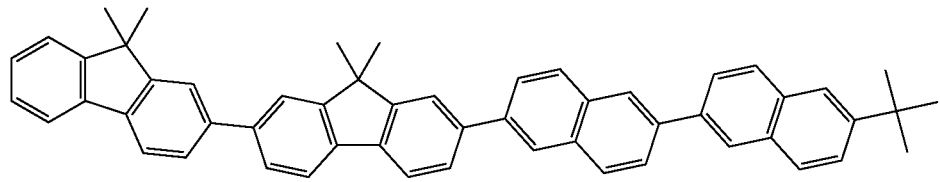
A-24
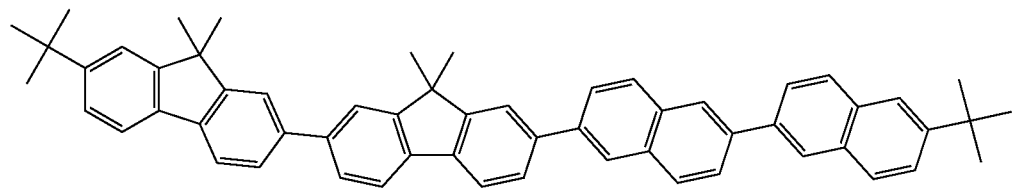
A-25
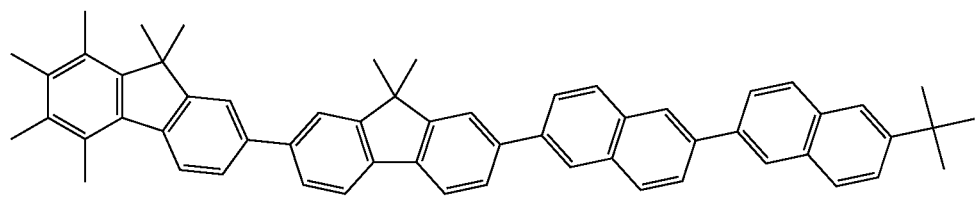
A-26
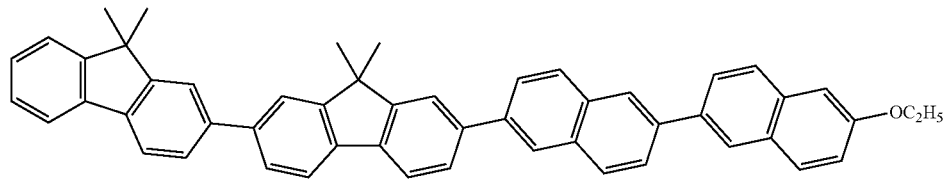
A-27

-continued
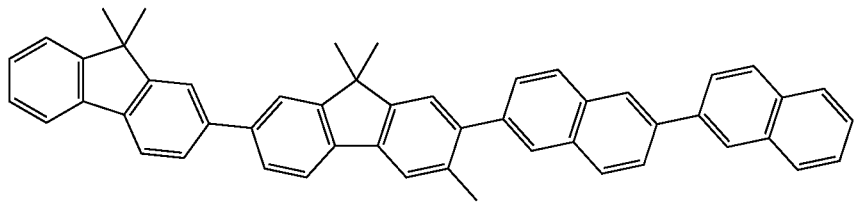
A-28
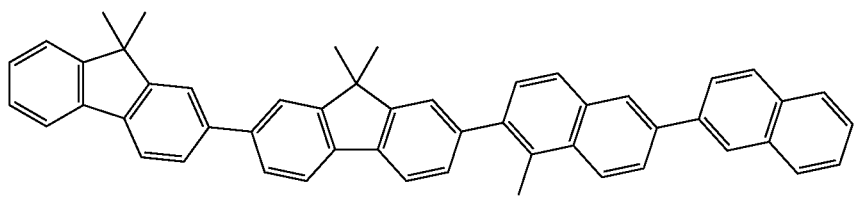
A-29
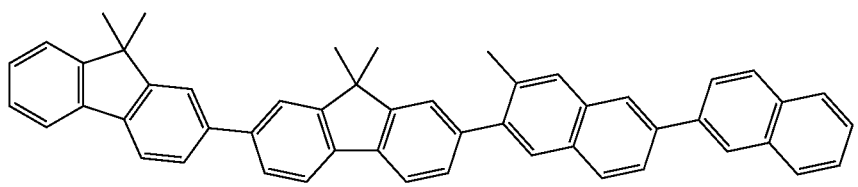
A-30
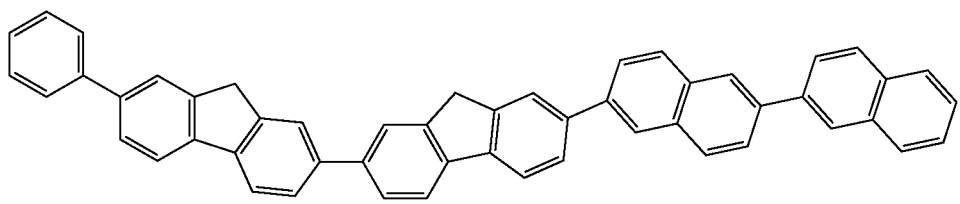
B-01
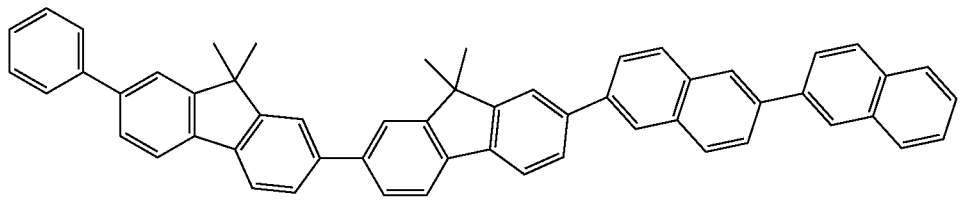
B-02
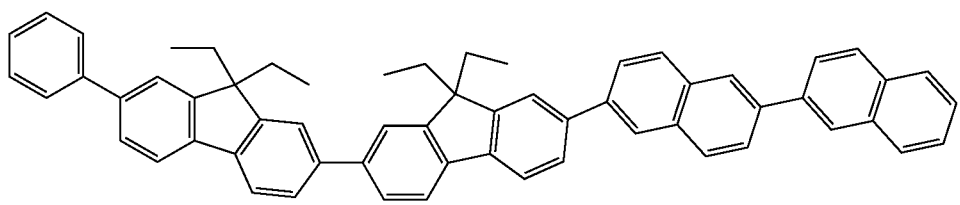
B-03
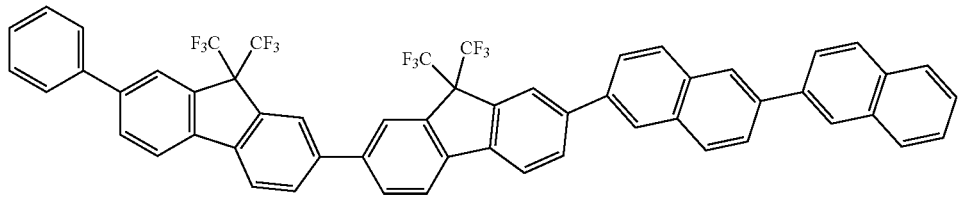
B-04
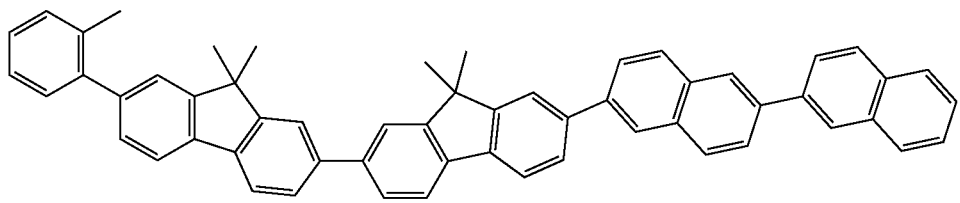
B-05

-continued
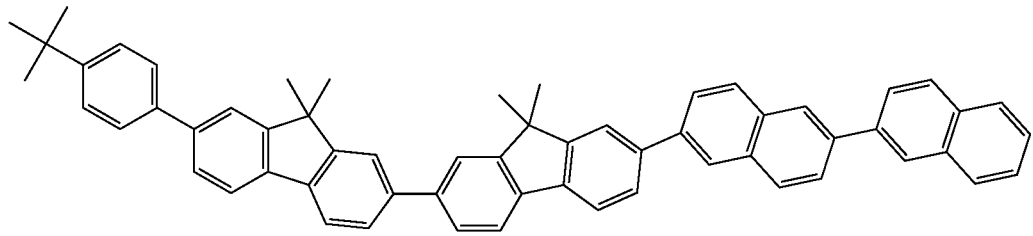
B-06
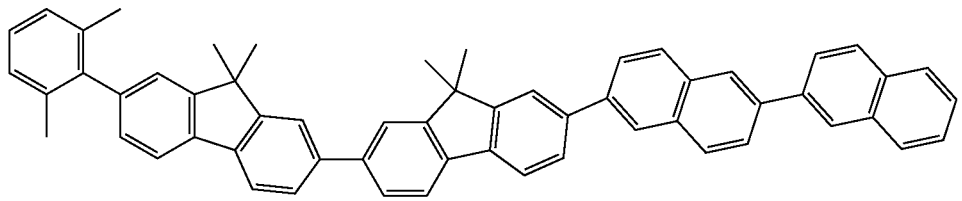
B-07
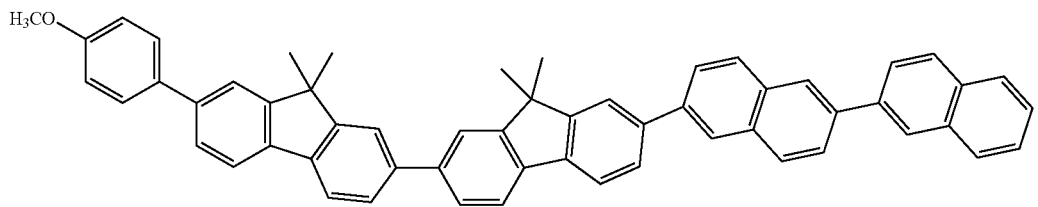
B-08
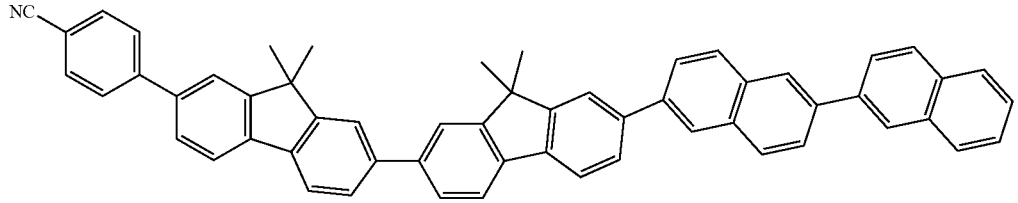
B-09
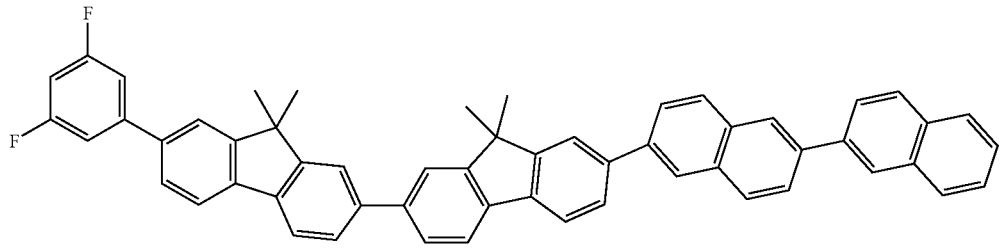
B-10
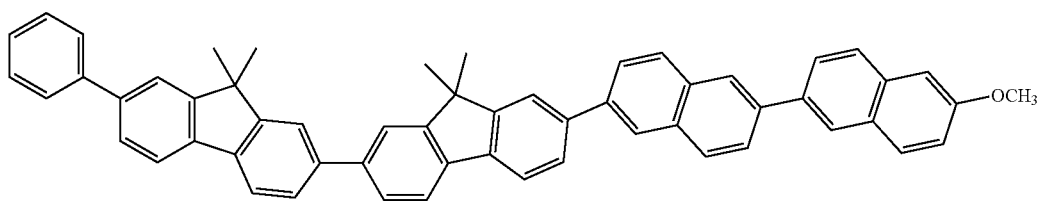
B-11
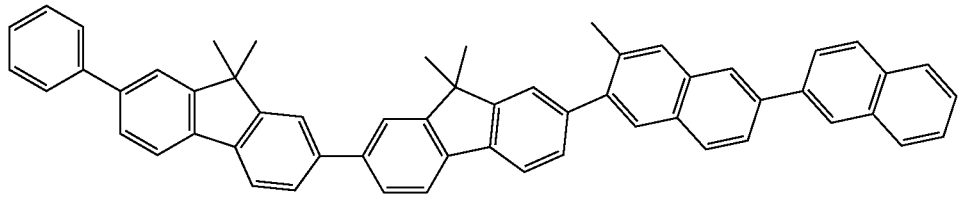
B-12

-continued
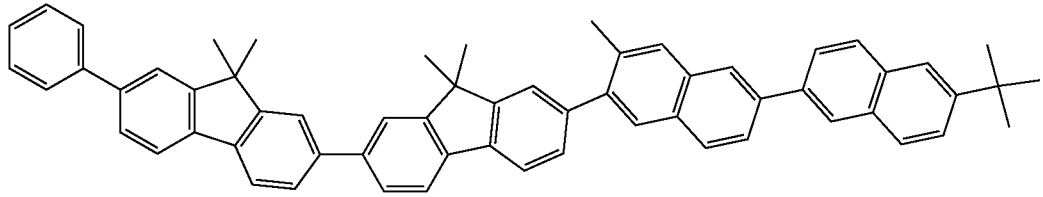
B-13
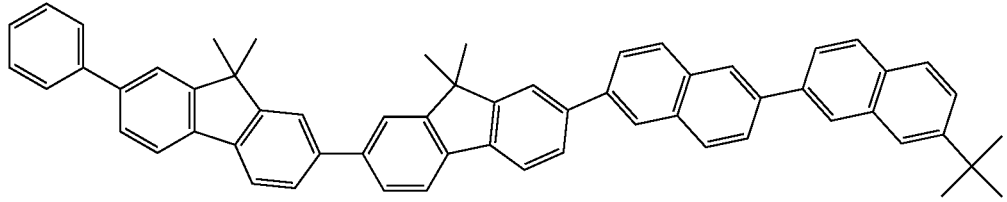
B-14
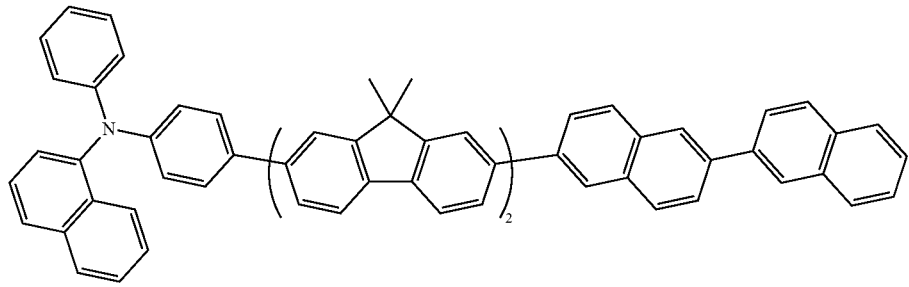
B-15
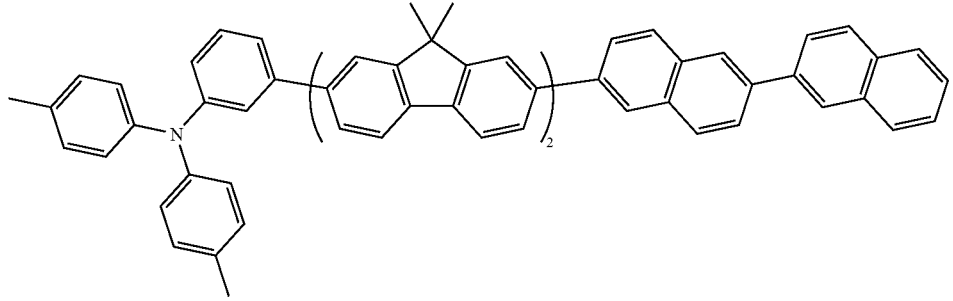
B-16
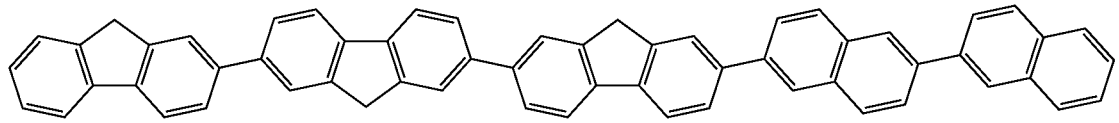
B-17
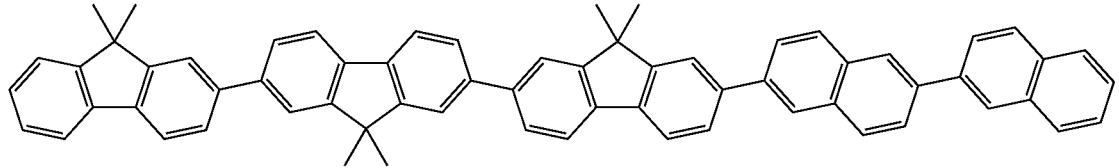
B-18
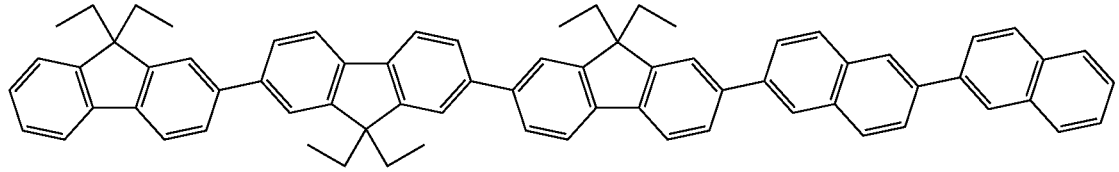
B-19

-continued
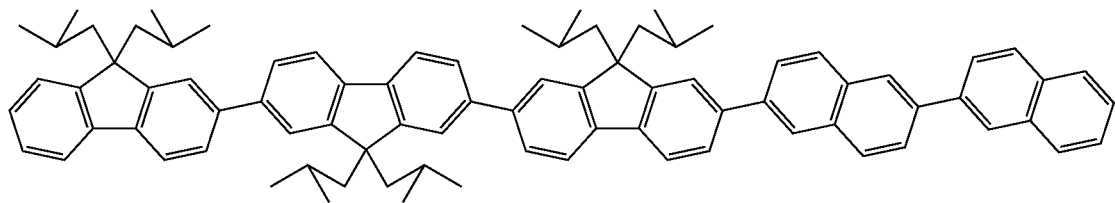
B-20
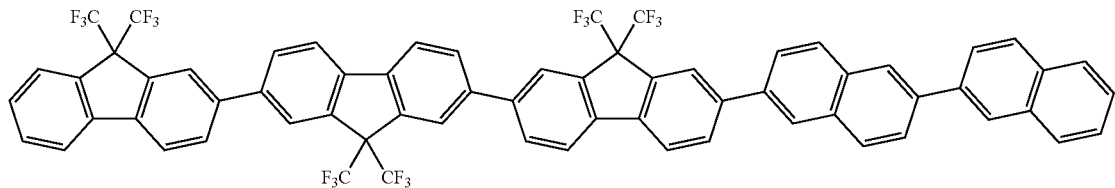
B-21
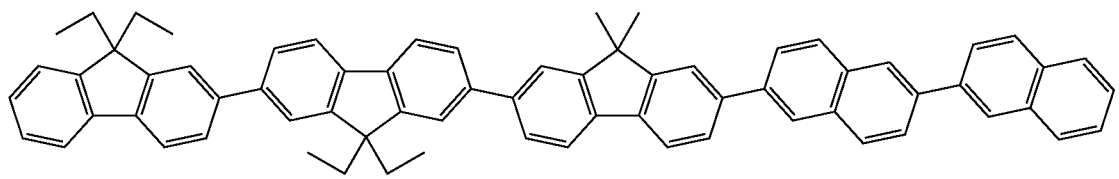
B-22
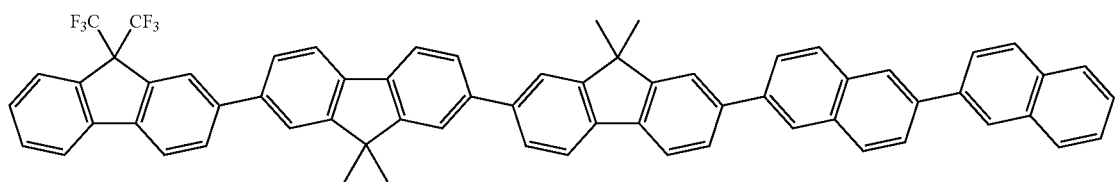
B-23
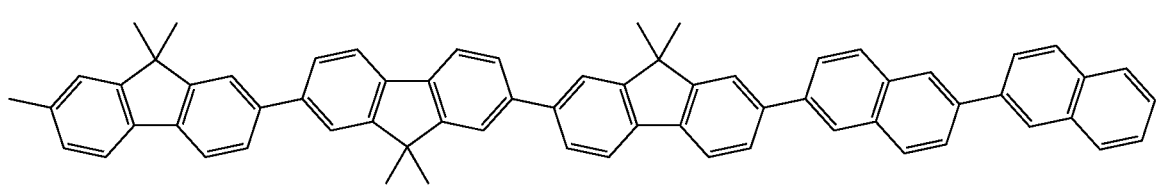
B-24
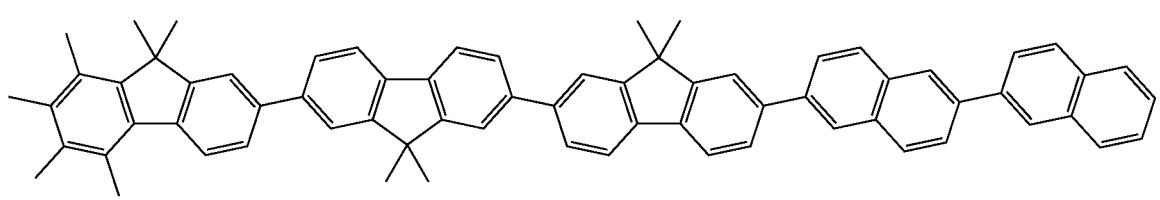
B-25
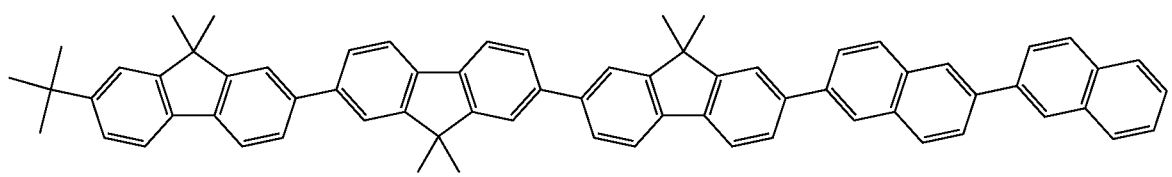
B-26
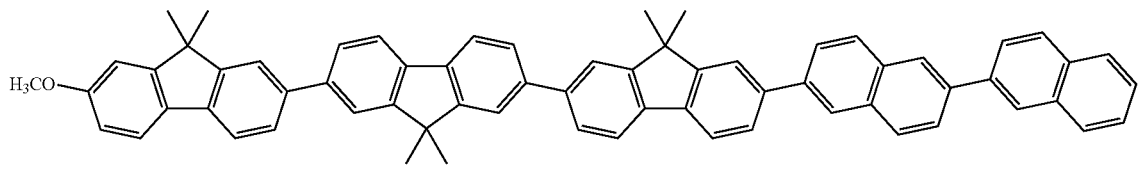
B-27

-continued
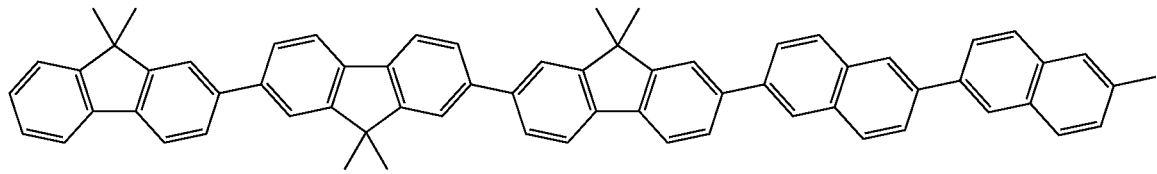
B-28
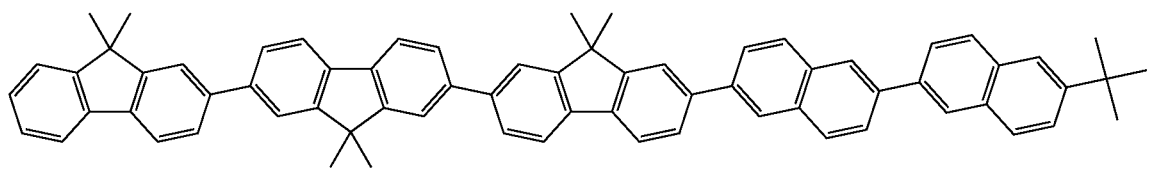
B-29
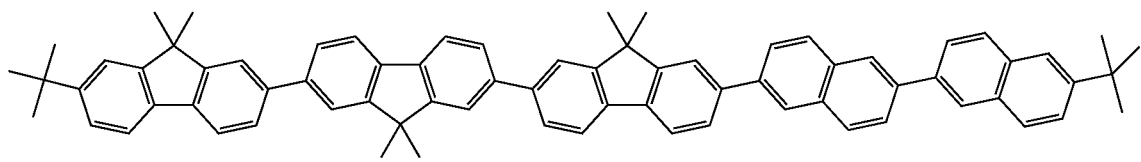
B-30
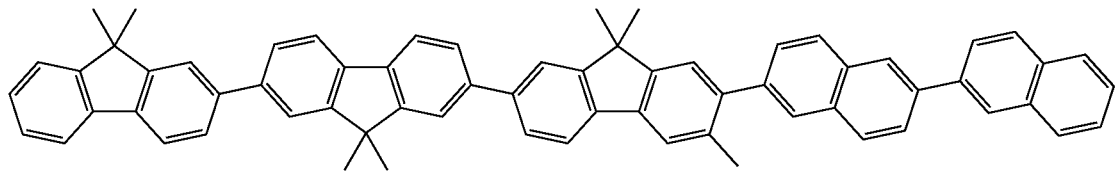
B-31
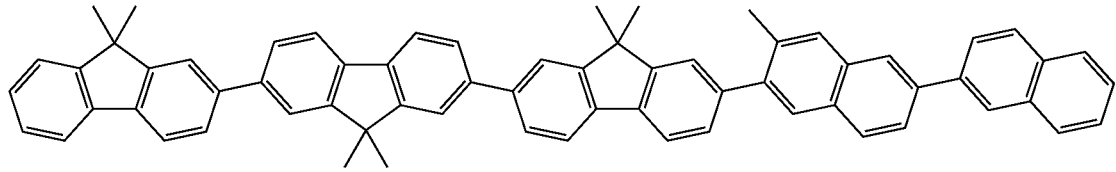
B-32
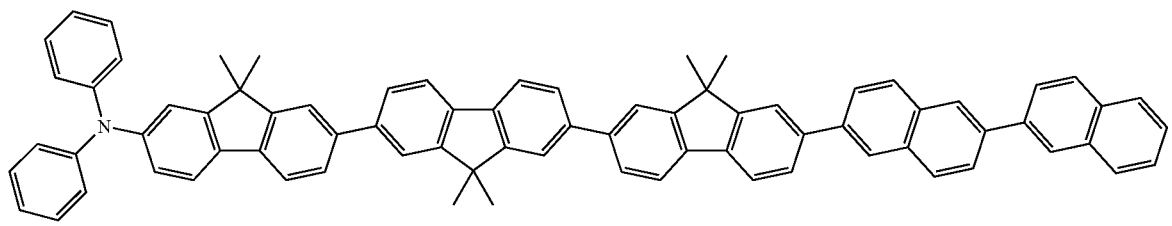
B-33
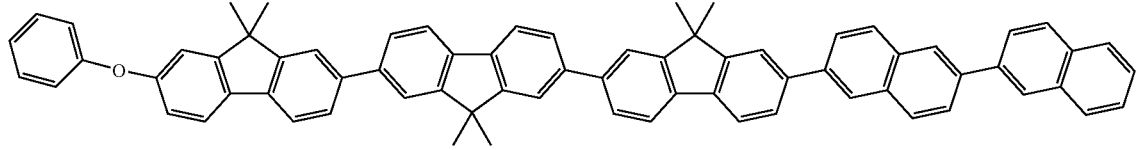
B-34
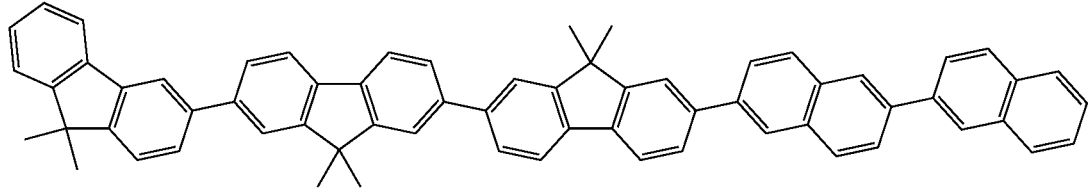
B-35

-continued
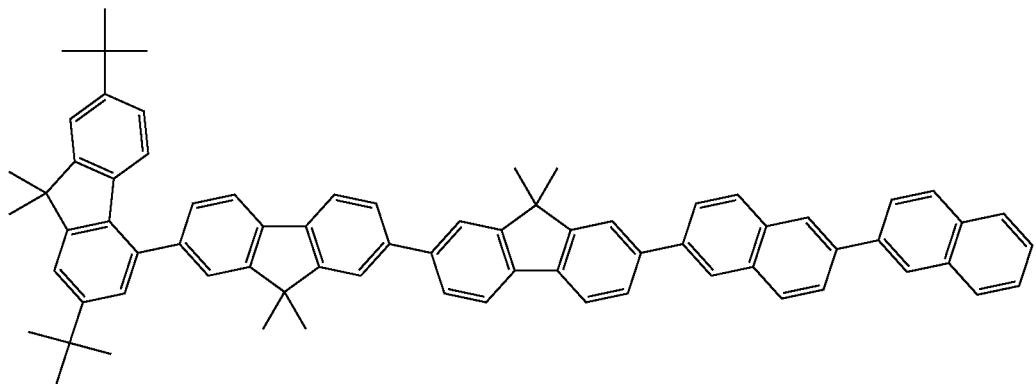
B-36
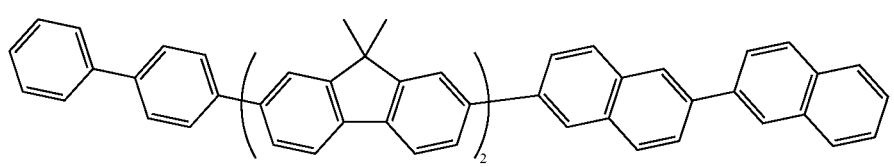
C-01
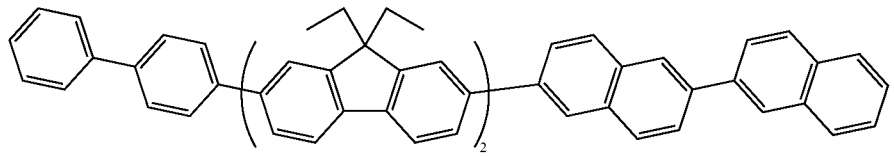
C-02
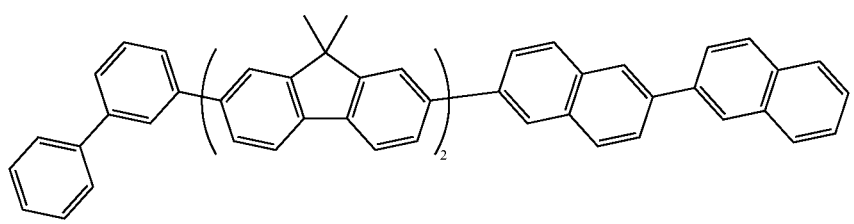
C-03
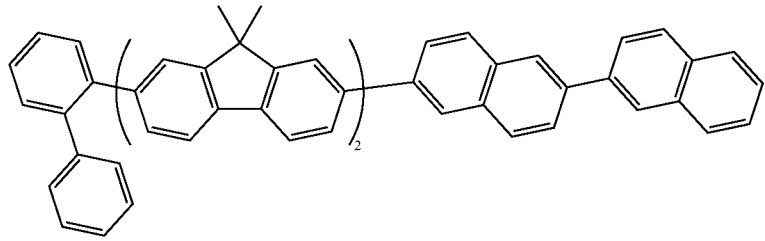
C-04
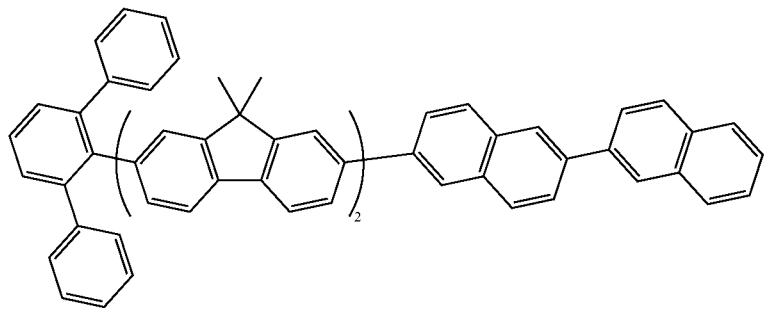
C-05

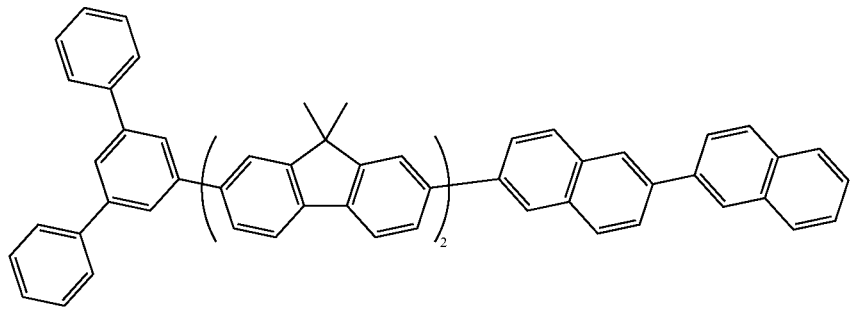
C-06
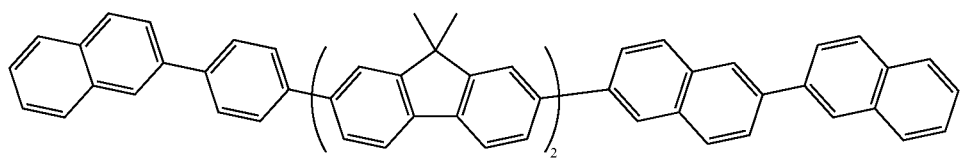
C-07
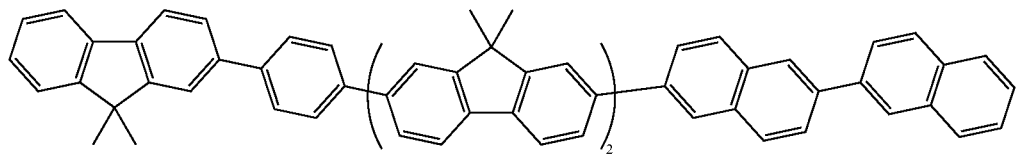
C-08
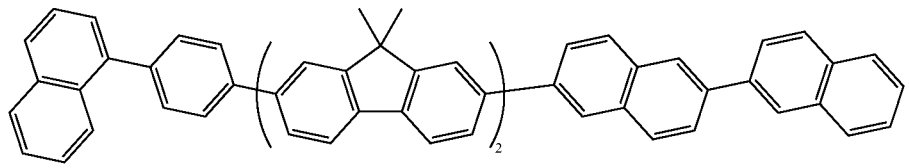
C-09
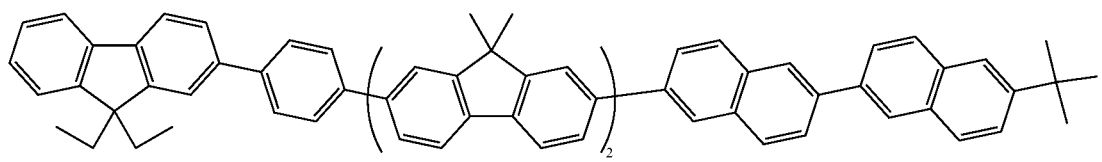
C-10
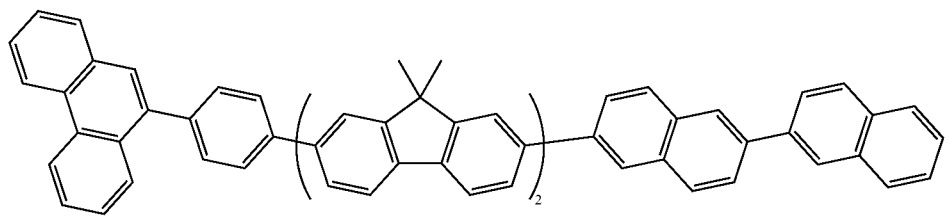
C-11
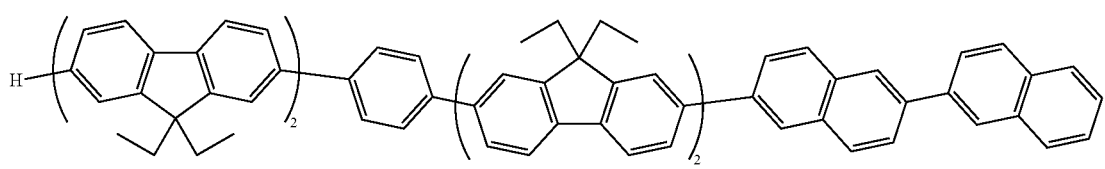
C-12
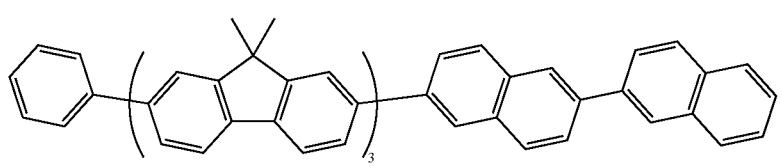
C-13

-continued
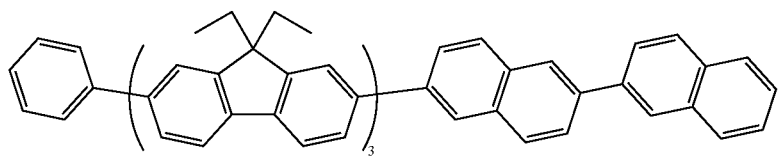
C-14
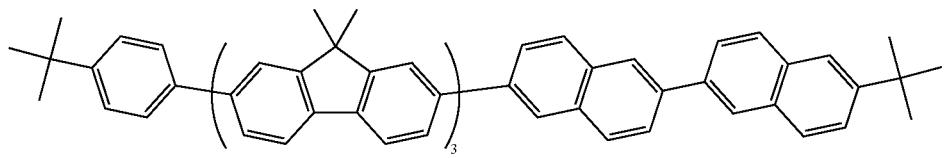
C-15
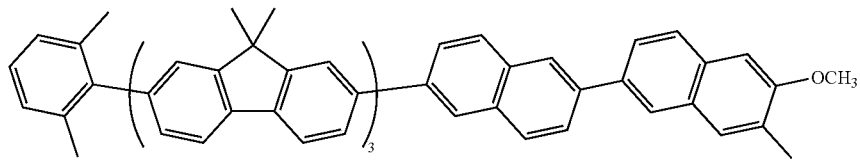
C-16
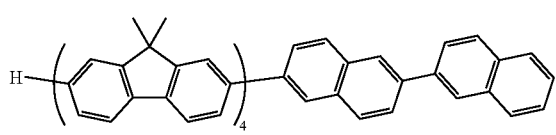
C-17
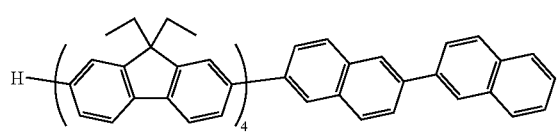
C-18
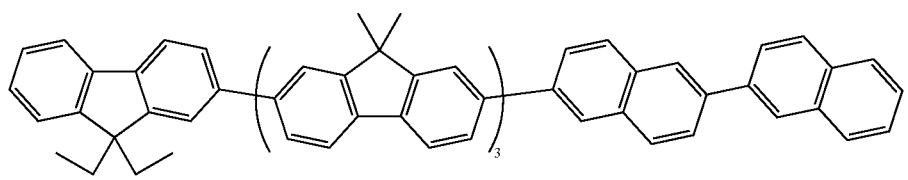
C-19
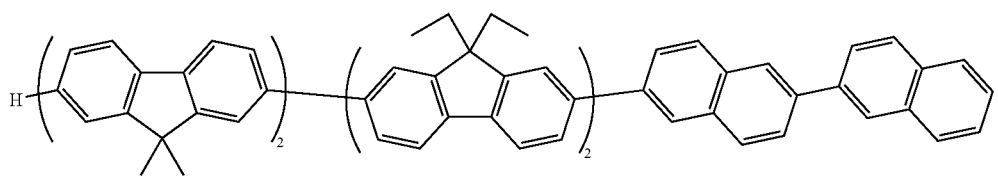
C-20
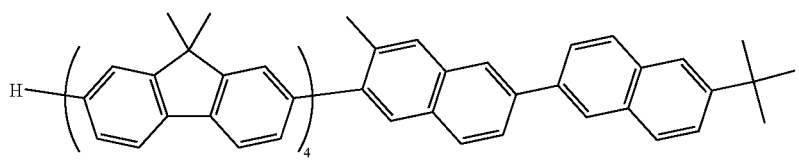
C-21
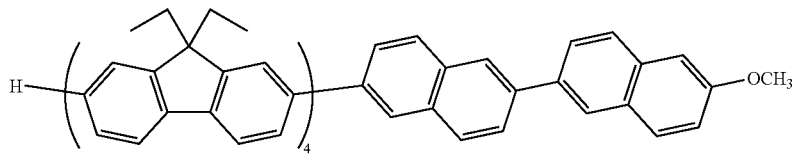
C-22
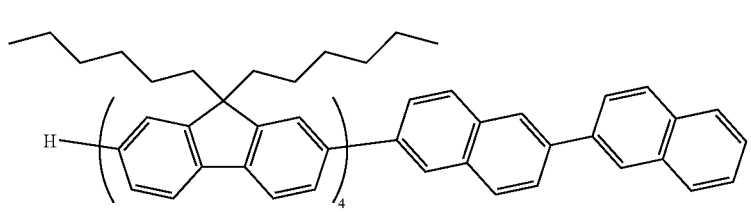
C-23

-continued
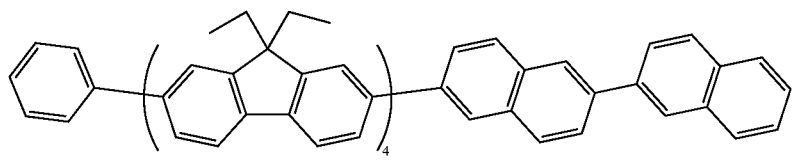
C-24
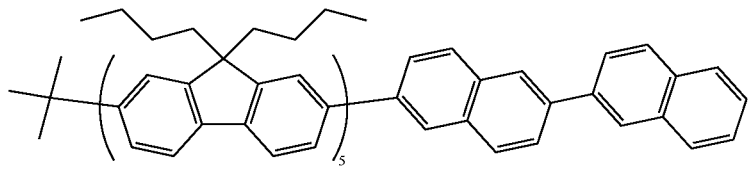
C-25
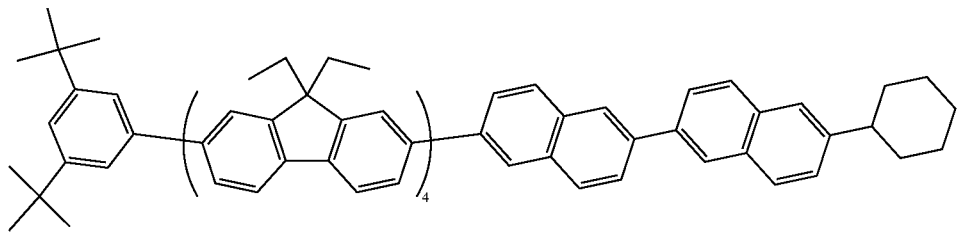
C-26
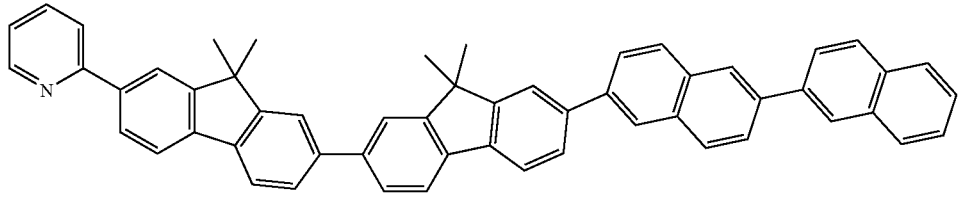
D-01
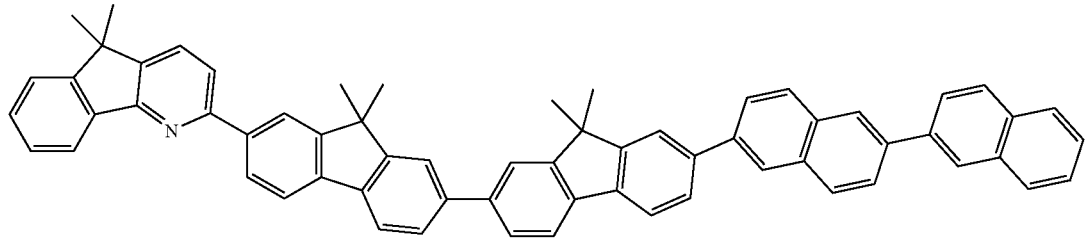
D-02
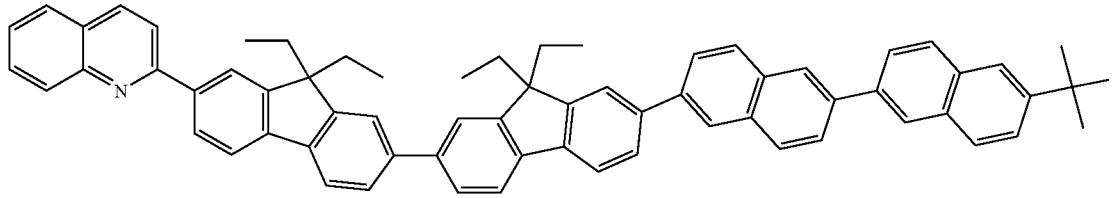
D-03
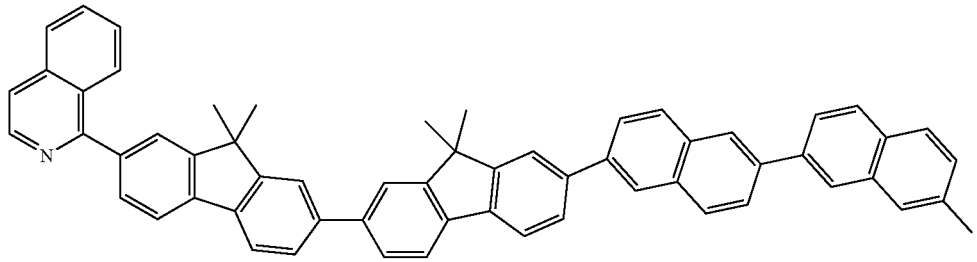
D-04

-continued

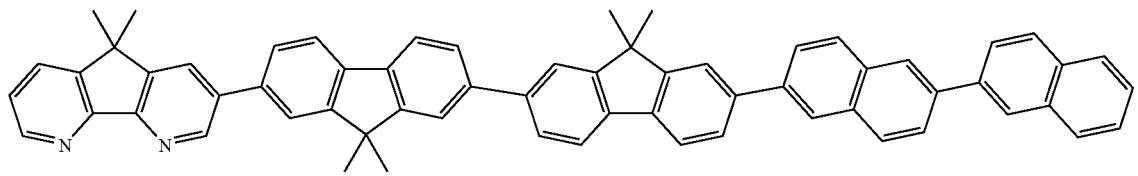

D-05

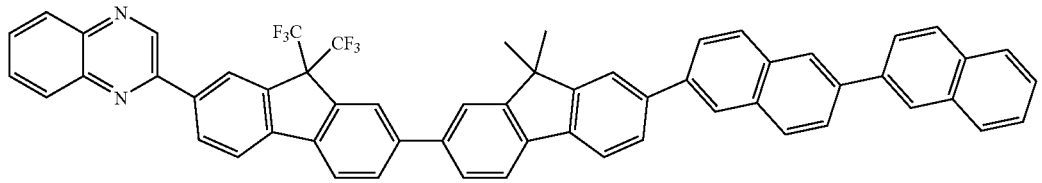

D-06

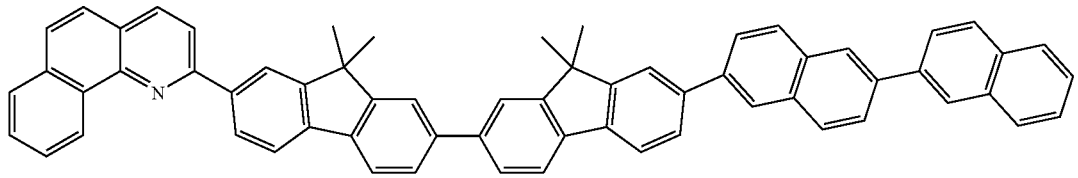

D-07

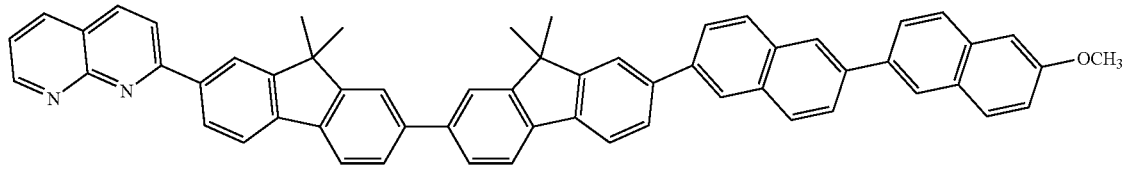

D-08

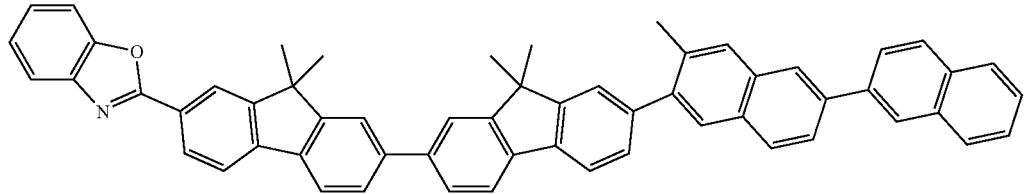

D-09

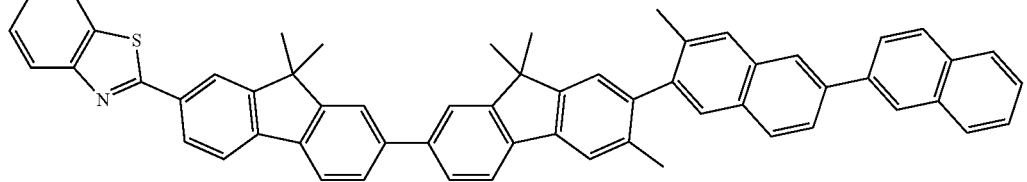

D-10

Next, the organic light emitting element of the present invention is described in detail.

The organic light emitting element of the present invention includes an anode, a cathode and a layer containing organic compounds sandwiched between the anode and the cathode. Either one of the anode and the cathode is transparent or semi-transparent. The organic light emitting element of the present invention is preferably an electroluminescence element which emits a light when a voltage is applied between the anode and the cathode.

Hereinbelow, the organic light emitting element of the present invention is described in detail referring to the drawings.

First, reference numerals in the drawings are described. Numeral 1 stands for a substrate, 2 for an anode, 3 for a light emitting layer, 4 for a cathode, 5 for a hole transport layer, 6 for an electron transport layer, 10, 20 and 30 each for an organic light emitting element, 40 and 60 each for a display apparatus. 41 stands for a scanning signal driver, 42 for an information signal driver, 43 for a current supply source, 44 and 50 each for pixel circuit, 51 for a first thin-film transistor (TFT), 52 for a condenser ($C_{add}$), 53 for a second thin-film transistor (TFT), 61 for a substrate, 62 for a moisture-proof layer, 63 for a gate electrode, 64 for a gate insulator film, 65 for a semiconductor film, 66 for a drain electrode, 67 for a source electrode, 68 for a TFT element, 69 for an insulating film, 70 for a contact hole (through-hole), 71 for an anode, 72 for an organic layer, 73 for a cathode, 74 for a first protective layer and 75 for a second protective layers, respectively.

FIG. 1 is a cross-sectional view illustrating a first embodiment of the organic light emitting element of the present invention. The organic light emitting element 10 in FIG. 1 has an anode 2, a light emitting layer 3 and a cathode 4 sequentially on a substrate 1. This organic light emitting element 10 is effective when a light emitting layer 3 is constituted of an organic compound having all of the functions of hole transport capability, electron transport capability and light emitting capability. The light emitting layer 3 may be constituted of a mixture of two or more organic compounds having either one of the functions of hole transport capability, electron transport capability and light emitting capability.

Figure 2:
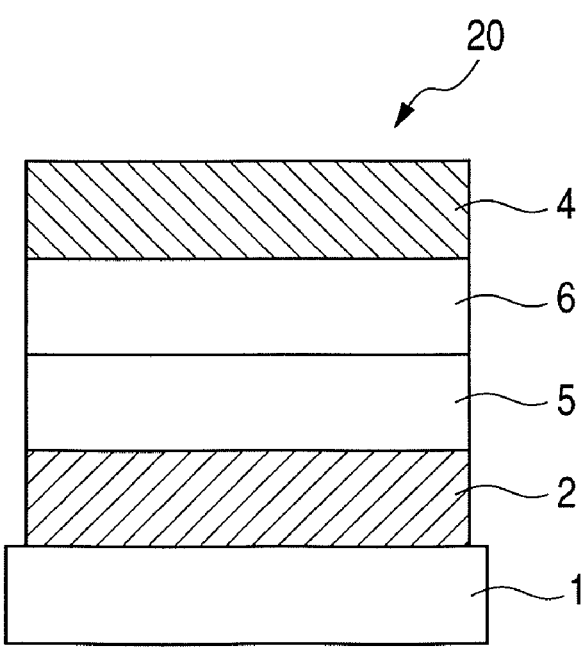
FIG. 2 is a cross-sectional view illustrating a second embodiment in the organic light emitting element of the present invention.

FIG. 2 is a cross-sectional view illustrating a second embodiment of the organic light emitting element of the present invention. The organic light emitting element 20 in FIG. 2 has an anode 2, a hole transport layer 5, an electron transport layer 6 and a cathode 4 sequentially on a substrate 1. In this organic light emitting element 20, it is preferable to use a light emitting organic compound having either one of hole transport capability and electron transport capability and an organic compound having only one of electron transport capability or hole transport capability electron transport capability in combination. In the organic light emitting element 20, either one of the hole transport layer 5 and the electron transport layer 6 also functions as a light emitting layer.

Figure 3:
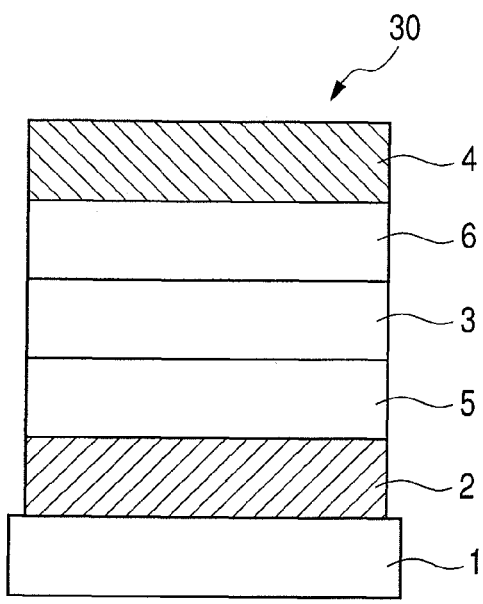
FIG. 3 is a cross-sectional view illustrating a third embodiment in the organic light emitting element of the present invention.

FIG. 3 is a cross-sectional view illustrating the third embodiment of the organic light emitting element of the present invention. The organic light emitting element 30 in FIG. 3 has a light emitting layer 3 inserted between a hole transport layer 5 and an electron transport layer 6 in the organic light emitting element 20 of FIG. 2. In this organic light emitting element 30, functions of carrier transportation and light emission are separated, and therefore, the element can be used by suitably combining organic compounds having respective one of hole transport capability, electron transport capability and light emission capability. On this account, freedom in selecting materials extremely increases and various kinds of organic compounds differing in emission wavelength can be used, and diversification of the color phase of the emitted light hue is enabled. Furthermore, it is enabled to enhance the light emitting efficiency by effectively confining each carriers or excitons in the central light emitting layer 3.

A hole injection layer may be also inserted between the anode 2 and the hole transport layer 5 in the organic light emitting element 30 of FIG. 3. This configuration has an effect of improving the close contact of the anode 2 and the hole transport layer 5 or hole injection properties and thus it is effective for lowering the driving voltage.

Furthermore, in FIG. 3, a layer (hole blocking layer, exciton blocking layer) which hinders holes or excitons from going through to the side of the cathode layer 4 may be inserted between the light emitting layer 3 and the electron transport layer 6. Use of a compound having a very high ionization potential as a constitution material of the hole blocking layer or exciton blocking layer is effective for improving the light emitting efficiency.

However, FIGS. 1, 2 and 3 inherently illustrate basic element constitutions and the constitution of the organic light emitting element which uses the binaphthyl compound of the present invention is not limited to these. For example, various layer constitutions including providing an insulating layer on the interface between the electrode and the organic layer, providing an adhesive layer or an interference layer, forming a hole transport layer with two layers different in ionization potential or using a light emitting layer as a laminate structure having two or more layers can be adopted.

In the organic light emitting element of the present invention, at least one binaphthyl compound of the present invention is contained in a layer formed of an organic compound. Here, the binaphthyl compound of the present invention contained in one layer may be a single compound or a combination of two or more compounds.

The layer formed of an organic compound which contains a binaphthyl compound of the present invention is specifically the light emitting layer 3, the hole transport layer 5 or the electron transport layer 6 shown in FIGS. 1, 2 and 3. It is preferably the light emitting layer 3.

The light emitting layer 3 may be composed of binaphthyl compound of the present invention alone but the layer 3 is preferably composed of a host and a guest. Preferably, the binaphthyl compound of the present invention is used as a host. More preferably, it is a host for a phosphorescence emitting compound used as a guest, and still further preferably it is a host for a red phosphorescence emitting light compound used as a guest.

Here, compounds preferable as a phosphorescence emitting compound are metal complexes such as an iridium complex, a platinum complex, a rhenium complex, a copper complex, a europium complex and a ruthenium complex. More preferably, it is an iridium complex whose intense phosphorescence emission is known. The light emitting layer may also include two or more phosphorescence emitting compounds for the purpose of helping the transportation of excitons and carriers, for instance.

Specific structural formulas of the metal complexes which function as red phosphorescence emitting compounds are shown below in the following list but, needless to say, the present invention is not limited to these.

TABLE 1

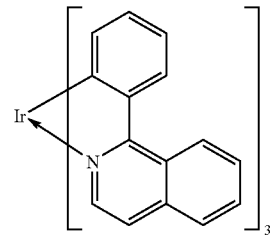

L01

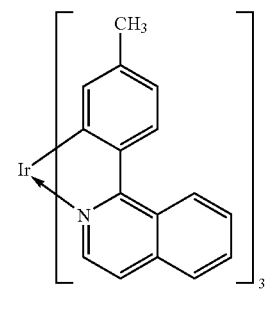

L02

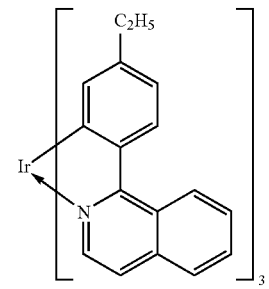

L03

TABLE 1-continued
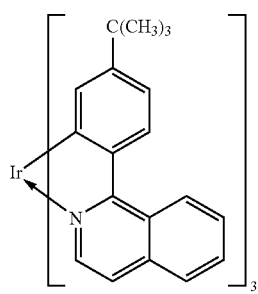
L04
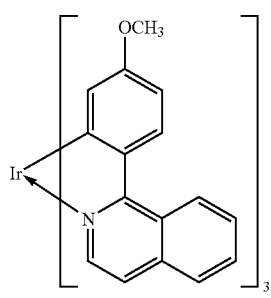
L05
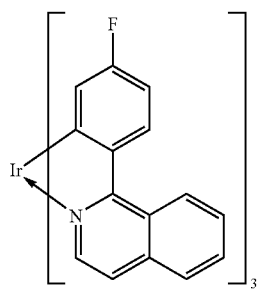
L06
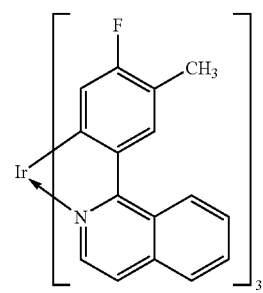
L07
TABLE 1-continued
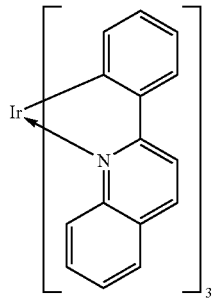
L08
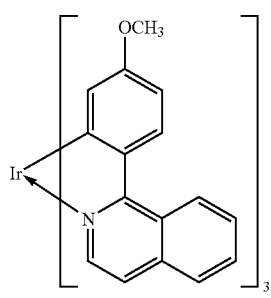
L09
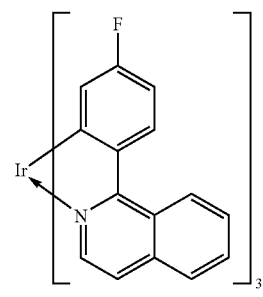
L10
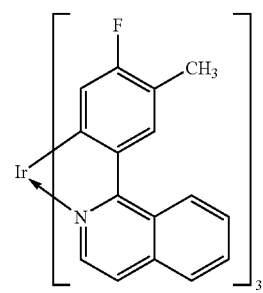
L11

TABLE 1-continued
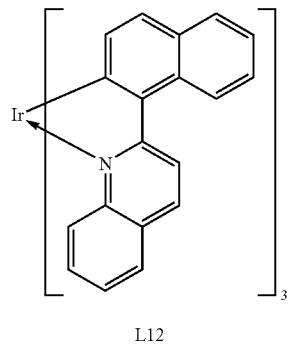
L12
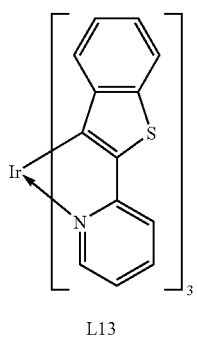
L13
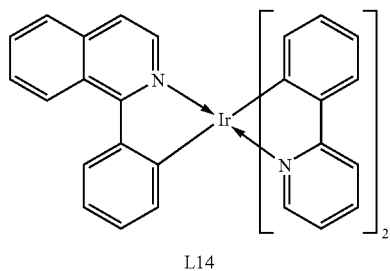
L14
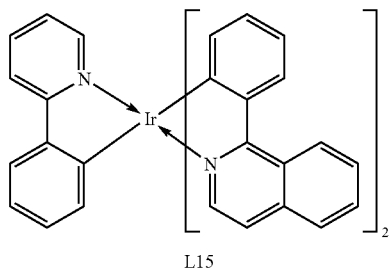
L15
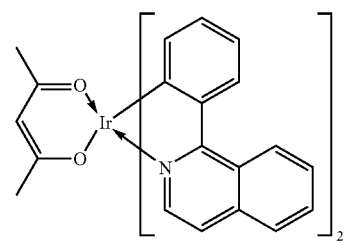
L16
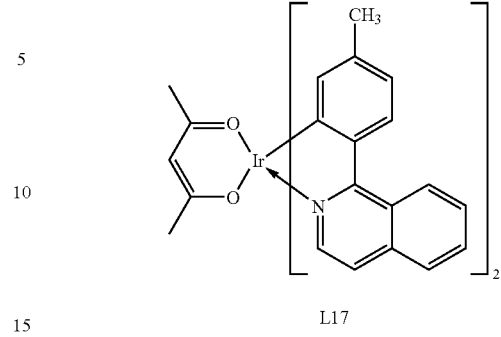
L17
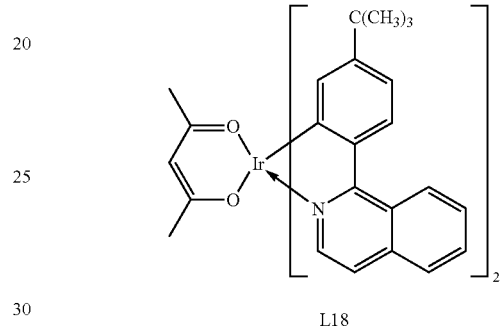
L18
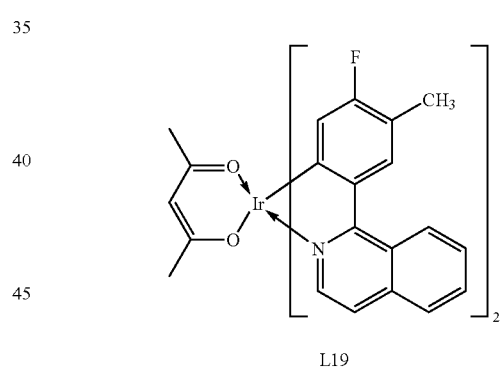
L19
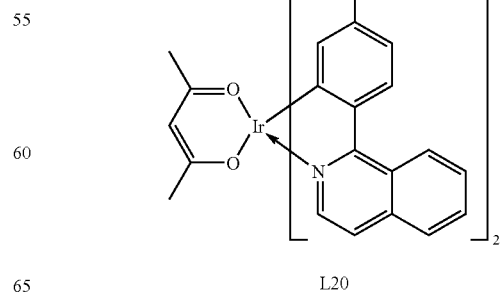
L20

TABLE 1-continued

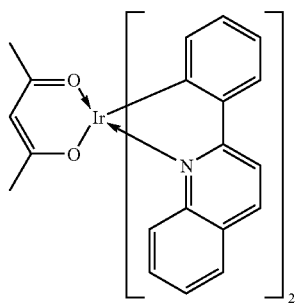

L21

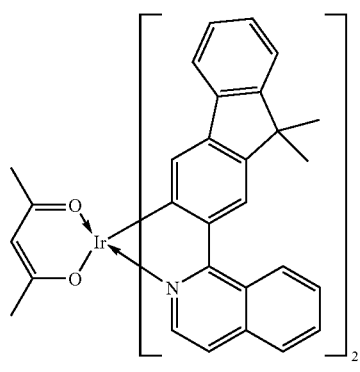

L22

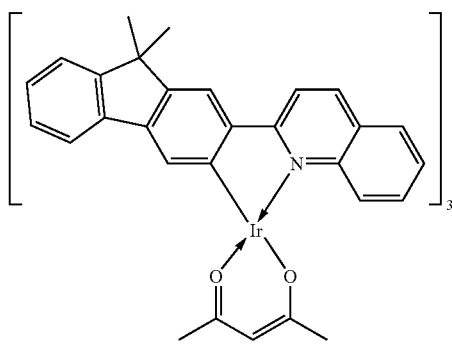

L23

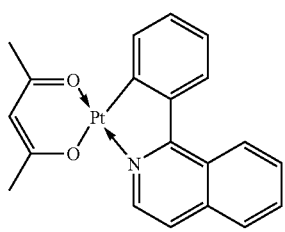

L24

The concentration of the guest to the host is 0.01 wt % to 50 wt % based on the total weight of the constitution materials of the light emitting layer 3, and preferably 1 wt % to 20 wt %. Particularly when the guest is a phosphorescence emitting compound, the concentration of the guest is preferably 15 wt % or less so as to prevent triplet-triplet annihilation. The guest may be contained uniformly in the whole layer which is composed of a host, or contained with a concentration gradient. Alternatively, the guest may be contained partially in a specific area to provide an area containing no guest in the host layer.

Preferably the light emitting layer of the organic light emitting element is constituted of a host and a guest as above. The guest as mentioned here is a compound which plays a main role in the emission of light in the light emitting layer. On the other hand, the host is a compound present as a matrix around the guest in the light emitting layer and it is a compound which mainly plays a role in the transportation of the carriers and supply of excitation energy to the guest. When the light emitting layer of the organic light emitting element is constituted of a host and a guest which transport carriers, the main process for achieving emission of light includes some steps as follows: (1) Transportation of electrons/holes in the light emitting layer (2) Generation of excitons of the host (3) Transfer of excitation energy between the host molecules (4) Transfer of excitation energy from the host to the guest.

Energy transfer and emission of light in each step occur in competition with various deactivation processes.

Needless to say, it is necessary to increase luminescence quantum yield of the luminescence center material itself so as to improve the luminescence efficiency of the organic light emitting element. Meanwhile, how to achieve efficient host-host or host-guest energy transfer is an important issue. In addition, although the reason why light emission deteriorates by the application of electricity to the organic light emitting element has not been elucidated at present, it is assumed to be related at least to the change in the environment of the light emitting material which change is attributable to the luminescent center material itself or the molecules therearound. It is also supposed that the deterioration of the quality of the amorphous film by crystallization and the deterioration with time of the organic layer by the electricity are part of the reasons for the deterioration of the light emission of the organic light emitting element.

Furthermore, it is supposed that one of the reasons for deterioration of the light emission due to the application of electricity may be failure in the balance of hole electric current and electronic electric current (carrier balance) in the light emitting layer. When the amount of carrier injected to the light emitting layer and the amount of carrier transported in the light emitting layer are significantly different between the both carriers, the carrier recombination area concentrates on the interface between the light emitting layer and the carrier transport layer, and the light emitting may only locally occur. In this case, electricity applied for a long time may produce carrier accumulated area in the vicinity of the interface between the light emitting layer and the carrier transport layer. This makes material deterioration in the level of molecular structure to be liable to occur in the luminescent center material or the molecules therearound which highly possibly leads to deterioration of the light emission.

Relations between the host and the guest are particularly important for carrier balance here. That is, it is necessary to sufficiently consider relative relations in terms of level between HOMO level and LUMO level of the guest and the host. It is further necessary to consider the following points as to the amount of injected holes and injected electrons. That is, as for the amount of injected holes, it is necessary to consider the hole injection barrier generated by the difference between the HOMO level of the hole transport layer and the HOMO level of the host of the light emitting layer. As for the amount of injected electrons, it is necessary to consider the barrier against electron injection generated by the difference between the LUMO level of the electron transport layer and the LUMO level of the host of the light emitting layer. Therefore, comprehensive molecular design of a compound which functions as the host of the light emitting layer should be performed considering relations of the guest of the light emitting layer and transportation layers for the both carriers which sandwich the light emitting layer.

In the meantime, the binaphthyl compound of the present invention having a 2,2'-binaphthyl type structure has a characteristic planeness and straightness. On this account, the compound shows high carrier transport capability in the state of an amorphous film. That is, the planeness possessed by the 2,2'-binaphthyl type structure promotes a large π-orbital interaction between the molecules and facilitates the giving and receiving of the carrier between the molecules. In addition, it is considered that the straightness possessed by 2,2'-binaphthyl type structure lengthens the π-conjugate length in a molecule and enables very fast carrier conduction in the molecule in a conducting wire manner over a long distance. Improvement in both intermolecular and intramolecular carrier conductivities provided by 2,2'-binaphthyl type structure contributes to high carrier transport capability in the amorphous film state. Thus, both the hole and electron carriers can be transported effectively without stress by an excessively large applied voltage when the binaphthyl compound of the present invention is used as the host of the light emitting layer.

On the other hand, even if it is a binaphthyl compound, it is very likely that carrier transport capability deteriorates and the effect mentioned above cannot be exhibited sufficiently by 1,1'-binaphthyl type structure. This is because planeness is significantly lost in the 1,1'-binaphthyl type structure since the hydrogen atoms present at peri-positions in the two naphthalene rings sterically hinder each other and thereby twist the two naphthalene rings.

The dihedral angle between the two naphthalene rings is 41.3° in 2,2'-binaphthyl and 69.10 in 1,1'-binaphthyl when structural optimization is performed by molecular orbital calculation for the two kinds of binaphthyl compounds shown below.

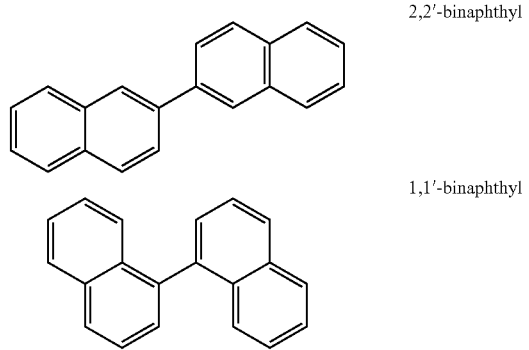

2,2'-binaphthyl 1,1'-binaphthyl

It is considered from this that the 2,2'-binaphthyl type structure has a higher planeness and exhibits higher carrier transport capability than the 1,1'-binaphthyl type structure.

The binaphthyl compound of the present invention has at least two fluorene rings linked directly to only one side of 2,2'-binaphthyl structure as an oligo(fluoren-2,7-diyl) group (oligofluorene moiety). This oligofluorene moiety has an elongated π conjugate plane but since substituent group at 9-position of the fluorene ring is out of the plane of the fluorene ring, there is no such a highly excessive planeness as making conspicuous of stacking of the molecules. Therefore, the binaphthyl compound of the present invention enhances straightness without excessively increasing the planeness of the whole molecule by introducing the oligofluorene moiety into a binaphthyl skeleton directly. It is supposed that this structure is a molecular structure which further develops the above-mentioned effect from a point of view of the carrier conduction.

Furthermore, the binaphthyl compound of the present invention is characterized in that it is asymmetric form as a whole molecule. On this account, the binaphthyl compound of the present invention has a high amorphous nature when formed into a film since it is low crystalline. Therefore, when the binaphthyl compound of the present invention is used as the host of the light emitting layer, an amorphous film which is stable even when it is driven for a long time can be maintained and deterioration in the light emission is reduced. In addition, the binaphthyl compound of the present invention has a high solubility in an organic solvent since it is low crystalline. On this account, the binaphthyl compound of the present invention is easily produced and purified.

In particular, a 2,2'-binaphthyl structure having two naphthalene skeletons linked to each other like a binaphthyl compound of the present invention is preferable since such a structure enhances amorphous nature of the film. In the oligo (naphthalen-2,6-diyl) structure having three or more naphthalene skeletons linked, the planeness of the molecule becomes excessively high, and all of crystallinity, stacking properties between molecules and difficulty in dissolution in an organic solvent become high. In that case, it becomes difficult to obtain a stable amorphous film and besides purification of the material by recrystallization and sublimation is made difficult, all of which are unpreferable.

Furthermore, the binaphthyl compound of the present invention can further improve solubility in an organic solvent and amorphous nature of the film and besides facilitates fine adjustment of physical properties such as carrier mobility by changing the kind of the substituent group at 9-position in the fluorene ring. For example, a compound having an ethyl group at the 9-position of the fluorene skeleton has a higher solubility and a lower carrier mobility as compared with a compound having a methyl group at the 9-position. However, it is not preferable to substitute the 9-position of the fluorene skeleton with an aryl group such as a phenyl group from a point of view of chemical stability since, in that case, radicals are more liable to be generated or the compound is more liable to be oxidized at the 9-position of the fluorene skeleton.

As described above, the binaphthyl compound of the present invention has high carrier transport capability and amorphous nature in the state as a film and therefore the compound is effective as the host of the light emitting layer which constitutes the organic light emitting element. Particularly the compound is effective as the host for the phosphorescence emitting compounds such as an iridium complex, which is a guest, in a red phosphorescence emitting element.

The binaphthyl compound of the present invention has an asymmetric structure combining oligo(fluoren-2,7-diyl) with 2,2'-binaphthyl. This molecule has CT (charge transfer) nature in a molecule, which can be elucidated by performing molecular orbital calculation. Here, the CT nature means that the HOMO and LUMO of the molecule are localized in different parts of the molecule separated from each other and when an electron transfer between HOMO-LUMO, electron movement over a sterically large distance is needed. In the case of the binaphthyl compound of the present invention, HOMO is localized centering at the oligo(fluoren-2,7-diyl) moiety whereas LUMO is localized centering at the 2,2'-binaphthyl moiety respectively. On this account, the binaphthyl compound of the present invention has CT nature.

In the meantime, generally other many aromatic hydrocarbon compounds show π-π* nature but do not show the CT nature like the binaphthyl compound of the present invention. Here, the π-π* nature means that HOMO and LUMO spread across the whole molecule and that there is no difference in the position where they are mainly present. It can be confirmed by molecular orbital calculation that various kinds of analogous compounds including fluorene and naphthalene, which are not the binaphthyl compound of the present invention, do not show CT nature but π-π* nature.

Furthermore, HOMO level is shallow (ionization potential is low) in the binaphthyl compound of the present invention due to the unique CT nature mentioned above, particularly because HOMO is mainly present centering at the oligofluorene moiety. This is developed by the unique CT nature which is attained only when all of the "asymmetric structure", "oligo (fluoren-2,7-diyl) skeleton" and "2,2'-binaphthyl skeleton" are simultaneously present as in the binaphthyl compound of the present invention.

Generally when the HOMO level of the guest of the light emitting layer is shallower than the HOMO level of the host, and the difference is large, hole trapping property in the light emitting layer increases and the hole mobility in the light emitting layer remarkably decreases. In such a case, the light emitting area is liable to be localized in the vicinity of the interface between the hole transport layer and the light emitting layer, and it is supposed that the light emission of the element remarkably deteriorates.

Furthermore, when the HOMO level of the host is deep, and there is a large hole injection barrier in the interface between the hole transport layer and the light emitting layer, localization of the light emitting area by the lack of amount of injected holes stated above becomes more remarkable, and deterioration in the emission of light becomes more significant.

In the meantime, many of the phosphorescence emitting metal complexes such as iridium complexes are generally the compounds having a shallow HOMO level. On this account, in the phosphorescence emitting element in which such a metal complex is the guests of the light emitting layer, localization of the light emitting area stated above is liable to occur in particular. Therefore, the host of light emitting layer for such a phosphorescence emitting element is required to have an improved carrier balance in the light emitting layer by increasing the amount of holes in the light emitting layer or decreasing the amount of electrons.

In particular, it is very effective to use a binaphthyl compound of the present invention, which has a shallow HOMO level, as the host of the light emitting layer in a red phosphorescence emitting element whose maximum light emission wavelength is 570 nm to 680 nm. Both of hole trapping property in the light emitting layer and hole injection barrier at the interface between the hole transport layer and the light emitting layer are reduced by using the binaphthyl compound of the present invention as a host. In addition, this improves carrier balance of holes and electrons in the light emitting layer and extends the light emitting area. Therefore, deterioration factors in the light emission such as carrier accumulation can be suppressed. Thus a long-life red phosphorescence emitting element having a high light emitting efficiency can be obtained.

Here, the reason why the present compound is effective in a red phosphorescence emitting element is that the triplet excitation level ($T_1$ level) of the binaphthyl compound of the present invention is higher than the $T_1$ level of the red phosphorescence emitting compound. Specifically, the triplet excitation level ($T_1$ level) of the binaphthyl compound of the present invention is around 2.1 eV. Generally in the phosphorescence emitting element, it is assumed to be necessary that the $T_1$ level of the host is higher than the $T_1$ level of the phosphorescence emitting guest which plays a main role in the emission of light in the light emitting layer so as to prevent deterioration in the light emitting efficiency by non-emission deactivation from the $T_1$ of the host. Among compounds consisting of a hydrocarbon, there can be exemplified no compounds which have a $T_1$ level not less than 2.0 eV and a shallow HOMO level not more than 5.7 eV other than the compounds which utilize CT nature like the binaphthyl compound of the present invention.

Alternatively, it is supposed that the CT nature possessed by the binaphthyl compound of the present invention causes some kind of effects on the carrier transport process of the host, the exciton generation process of the host and the process in which the excitation energy generated in the exciton generation process transfers to the phosphorescence emitting guest.

In the meantime, the binaphthyl compound of the present invention is effective as a host of the light emitting layer which constitutes a blue fluorescence emitting element. The high carrier transport capability and amorphous nature provided by the inventive binaphthyl compound are also effective as a host of the light emitting layer which constitutes a fluorescence emitting element. Since the binaphthyl compound of the present invention has a bandgap of around 3 eV and emits a strong deep blue light. Accordingly, it is suitable for the host of the light emitting layer of a blue fluorescence emitting element from the viewpoint of excitation energy transfer to a blue light emitting guest. Particularly, since the binaphthyl compound of the present invention has a shallow HOMO level, it is preferably used as a host of the blue fluorescence emitting layer for the purpose of improving carrier balance in the light emitting layer by increasing the amount of holes.

As stated above, the binaphthyl compound of the present invention is preferably used as a host contained in the light emitting layer of red phosphorescence emitting element or the light emitting layer of a blue fluorescence emitting element but the use thereof is not limited to these. Specifically, the binaphthyl compound of the present invention may be used as a guest in the light emitting layer of a blue fluorescence emitting element or constitution materials of the electron transport layer. Particularly, Example Compounds D-01 to D-10 contain heteroaromatic rings, which are hard to transport holes, in the molecule and therefore they may be used as constitution materials of the hole blocking layer.

As stated above, the organic light emitting element of the present invention comprises at least one binaphthyl compounds of the present invention in a layer constituted of an organic compound. Particularly, the binaphthyl compound of the present invention is used as a host of the light emitting layer. Here, in the organic light emitting element of the present invention, conventionally known low-molecular-weight and polymer hole transport compounds, light emitting compounds or electron transport compounds in addition to the binaphthyl compound of the present invention can be used together as required.

Examples of these compounds are listed below.

As hole injection transport materials, materials to which holes can be easily injected from the anode and which have a high hole mobility are preferable so as to enable to transport the injected holes to the light emitting layer. Examples of the low molecular and polymer materials having positive hole injection transport capability include triarylamine derivatives, phenylene diamine derivatives, stilbene derivatives, phthalocyanine derivatives, porphyrin derivatives, poly(vinylcarbazole), poly(thiophene) and the other conductive polymers but, needless to say, they are not limited to these.

Besides the binaphthyl compounds of the present invention and the phosphorescence emitting compounds stated above, examples of the light emitting materials mainly involved in light emission function include condensed ring compounds (for example, fluorene derivatives, pyrene derivatives, tetracene derivatives, 9,10-diphenyl anthracene derivatives, rubrene, etc.), quinacridone derivatives, coumarin derivatives, stilbene derivatives, organic aluminum complexes such as tris(8-quinolinolate) aluminum, organic beryllium complexes and polymer derivatives such as poly(phenylenevinylene) derivatives, poly(fluorene) derivatives, poly(phenylene) derivatives but, needless to say, they are not limited to these.

The electron injection transport materials can be arbitrarily selected from materials to which electrons can be easily injected from the cathode and which can transport the injected electrons to the light emitting layer and selection is performed in consideration of the balance with the hole mobility of the hole injection transport materials. Examples of the materials having electron injection transport capability include oxadiazole derivatives, oxazole derivatives, pyrazine derivatives, triazole derivatives, triazine derivatives, quinoline derivatives, quinoxaline derivatives, phenanthroline derivatives, organic aluminum complexes but, needless to say, they are not limited to these.

As anode materials, those having a work function as high as possible are preferable. For example, simple metal substances such as gold, platinum, silver, copper, nickel, palladium, cobalt, selenium, vanadium and tungsten, alloys combining these or metal oxide such as tin oxide, zinc oxide, indium oxide, indium tin oxide (ITO) and indium zinc oxide can be used. In addition, conductive polymers such as polyaniline, polypyrrol and polythiophene can be used. These electrode materials may be used as a single kind of substance alone or two or more kinds of them may be used together. The anode may be constituted of one layer or may be constituted of two or more layers.

On the other hand, as cathode materials, those having a low work function are preferable. Example thereof include simple metal substances such as alkali metals such as lithium, alkaline earth metals such as calcium, aluminum, titanium, manganese, silver, lead and chromium. Alloys combining simple metal substances can be also used. For example, magnesium-silver, aluminum-lithium, aluminum-magnesium, etc. can be used. Use of metal oxides such as indium tin oxide (ITO) is also possible. These electrode materials may be used as a single kind of substance alone or two or more kinds of them may be used together. The cathode may be constituted of one layer or may be constituted of two or more layers.

The substrate used in the organic light emitting element of the present invention is not particularly limited and nontransparent substrates such as metal substrates and substrates made of ceramics and transparent substrates such as glass, quartz and plastic sheets can be used. The color of the emitting light can be controlled using a color filter film, a fluorescent color conversion filter film, a dielectric reflection film, etc on the substrate.

In addition, a protective layer or a sealing layer can be provided on the produced elements for the purpose of preventing exposure to oxygen or moisture. Examples of the protective layer include inorganic material films such as such as a diamond film, metal oxides and metal nitrides, polymer films such as fluorine resins, polyethylene, silicone resins and polystyrene resins, and further photocurable resins. The substrates may be covered with glass, a gas impermeable film and a metal and the element in itself can be packaged with a suitable sealing resin.

As for the direction of taking out the light from the element, either one of bottom emission configuration (configuration to take out light from the substrate side) or top emission configuration (configuration to take out light from the other side of the substrate) is possible.

In the organic light emitting element of the present invention, the layer which contains a binaphthyl compound of the present invention and the layers composed of the other organic compounds are formed by the method shown below. Generally, a thin film is formed by vacuum deposition method, ionization vapor deposition method, sputtering, plasma or conventional coating method (for example, spin coating, dipping, cast method, LB method, ink-jet method, etc.) after dissolving the material in a suitable solvent. Among these, when a layer is formed by vacuum deposition method or a solution coating method, crystallization is hard to occur and the formed layer is excellent in stability with time. When a film is formed by a coating method, the material can be combined with a suitable binder resin to form a film.

Examples of the binder resin include polyvinylcarbazole resins, polycarbonate resins, polyester resins, ABS resins, acrylic resins, polyimide resins, phenol resins, epoxy resins, silicone resins, urea resins but it is not limited to these. These binder resins may be use as one single kind alone as a homopolymer or a copolymer or two or more kinds of them may be mixed and used. Additives such as a conventionally known plasticizer, antioxidant, ultraviolet ray absorbent may be used together as required.

The organic light emitting element of the present invention can be applied to the product which needs energy saving and high brightness. As applied examples, display apparatuses, light sources of a printer, lighting installations, backlights of a liquid-crystal display, etc. can be envisaged.

Examples of the display apparatus include a lightweight flat-panel display for energy saving and high visibility.

As a light source of a printer, for example, the laser light source part of a laser beam printer used widely at present can be replaced with an organic light emitting element of the present invention. Examples of a method for replacement include a method of arranging independently addressable organic light emitting elements in an array. Even if the laser light source part is replaced with an organic light emitting element of the present invention, imaging procedure is the same as before which is performed by a desired exposure on the photoconductive drum. The volume of the device can be greatly decreased by using an organic light emitting element of the present invention here.

As for the lighting installations and backlights, an energy-saving effect can be expected by using an organic light emitting element of the present invention.

Next, a display apparatus using an organic light emitting element of the present invention is described. The display apparatus of the present invention is described below in detail taking an example of active matrix display and referring to the drawings.

Figure 4:
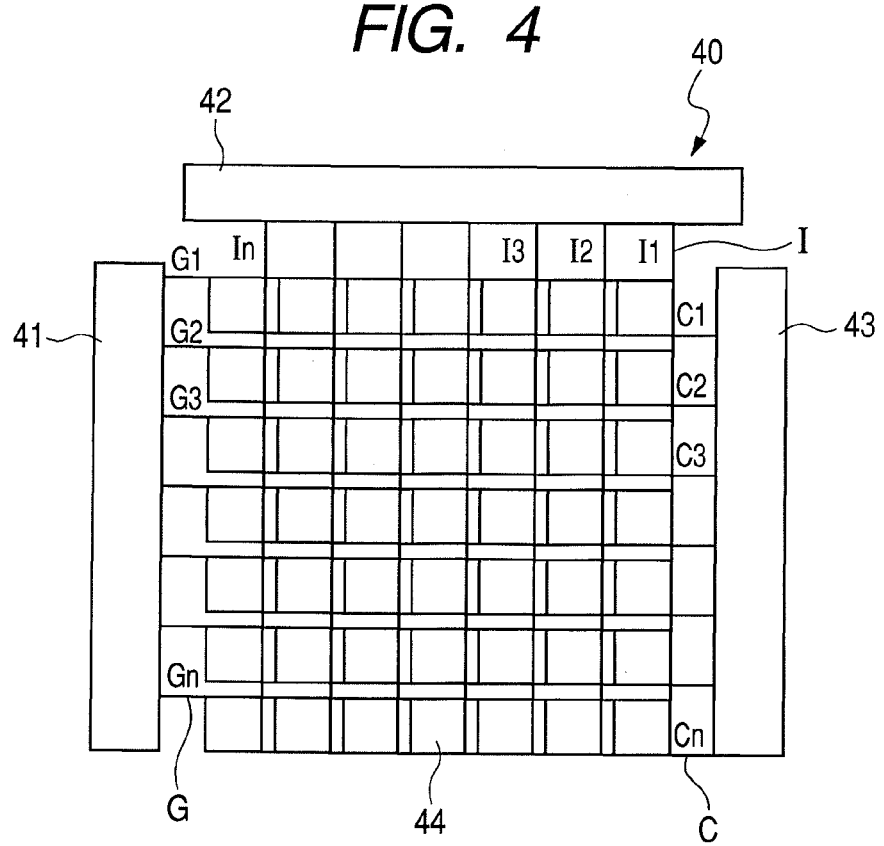
FIG. 4 is a view schematically illustrating a constitution example of a display apparatus including an organic light emitting element of the present invention and a driving unit.

FIG. 4 schematically illustrates a constitution example of a display apparatus which is one embodiment of the display apparatus and includes an organic light emitting element of the present invention and a driving unit. A display apparatus 40 of FIG. 4 includes a scanning signal driver 41, an information signal driver 42 and a current supply source 43 disposed therein, which respectively connects to gate select lines G, information signal lines I and electric current supply lines C. Pixel circuits 44 are disposed on the intersection points of gate select lines G and information signal lines I. The scanning signal driver 41 selects gate select lines G1, G2, G3, . . . , Gn sequentially, and in synchronization with this an image signal is applied to the pixel circuits 44 through either one of the information signal lines I1, I2, I3 . . . , In from the information signal driver 42.

Figure 5:
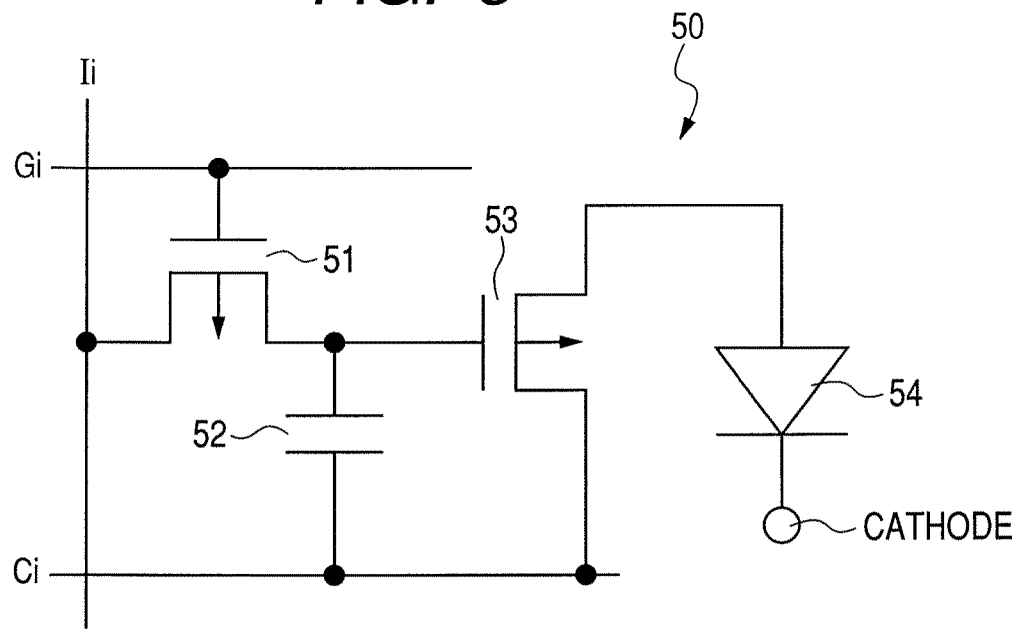
FIG. 5 is a circuit diagram illustrating a circuit which constitutes one pixel disposed in the display apparatus in FIG. 4.

The behavior of the pixels is described next. FIG. 5 is a circuit diagram illustrating a circuit which constitutes one pixel disposed in the display apparatus in FIG. 4. In the pixel circuit 50 of FIG. 5, when a select signal is applied on a gate select line G1, the first thin-film transistor (TFT1) 51 turns ON, and the image signal Ii is supplied to a condenser ($C_{add}$) 52 and determines the gate voltage of the second thin-film transistor (TFT2) 53. An electric current is supplied to an organic light emitting element 54 from a current supply line Ci according to the gate voltage of the second thin-film transistor (TFT2) (53). Here, the gate electric potential of the second thin-film transistor (TFT2) 53 is maintained to the condenser ($C_{add}$) 52 until the first thin-film transistor (TFT1) 51 is scanned and selected next. On this account, an electric current continues to flow into the organic light emitting element 54 until the next scanning is performed. This enables the organic light emitting element 54 to emit light all the time during one frame period.

Figure 6:
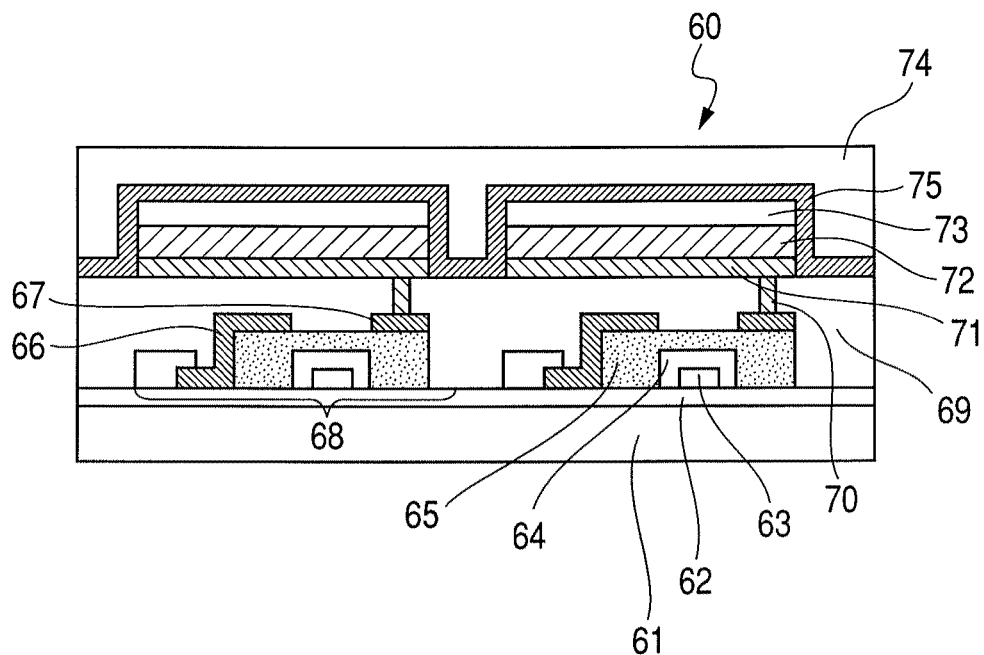
FIG. 6 is a schematic view illustrating an example of the sectional structure of a TFT substrate.

FIG. 6 is a schematic view illustrating an example of the sectional structure of the TFT substrate used in the display apparatus of FIG. 4. The details of the structure are described below while showing an example of the production process of the TFT substrate. When the display apparatus 60 of FIG. 6 is produced, a moisture-proof film 62 to protect members (TFT or an organic layer) to be formed thereon is coated at first on a substrate 61 such as the glass. As a material constituting the moisture-proof film 62, silicon oxide or a composite material of silicon oxide with silicon nitride is used. Then, a film of a metal such as Cr is formed by sputtering and a gate electrode 63 is formed by patterning the film in a predetermined circuit form. Subsequently, a film of silicon oxide is formed by plasma CVD method or catalytic chemical vapor phase deposition method (cat-CVD method) and a gate insulation film 64 is formed by patterning. Then a silicon film is formed by plasma CVD method (and annealed at a temperature not less than 290° C. depending on cases) and a semiconductor layer 65 is formed by patterning the film following the circuit form.

Furthermore, a drain electrode 66 and a source electrode 67 are provided on this semiconductor film 65 to form a TFT element 68 and a circuit shown in FIG. 5 is formed. Next, an insulation film 69 is formed on the upper part of this TFT element 68. Then a contact hole (through-hole) 70 is formed so that an anode 71 composed of a metal for the organic light emitting element and the source electrode 67 are connected.

A display apparatus 60 can be obtained by sequentially laminating a multi-layered or single-layered organic layer 72 and a cathode 73 on this anode 71. A first protective layer 74 and a second protective layer 75 may be provided on this occasion to prevent the deterioration of the organic light emitting element. Stable display with a good image quality even for a long time is enabled by driving the display apparatus using an organic light emitting element of the present invention.

The switching element is not particularly limited in the display apparatus mentioned above and a single crystal silicon substrate, an MIM element and an a-Si type can be applied easily.

EXAMPLES

Hereinbelow the present invention is specifically described by way of working examples. However, the present invention is not limited to these.

Example 1

Synthesis of Example Compound A-02

(1) Synthesis of Halogenated Compound X-20

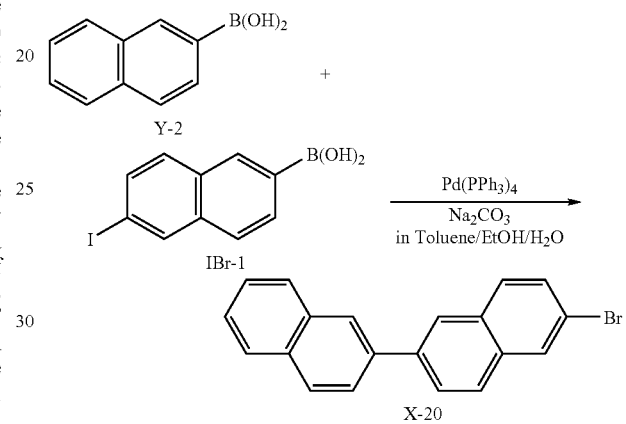

The reagents and the solvent shown below were charged to a 300-mL round-bottomed flask under nitrogen.
Boronate compound Y-2: 4.92 g (28.6 mmol)
Iodobromo compound IBr-1: 10.0 g (30.0 mmol)
Toluene: 100 mL
Ethanol: 50 mL Then, 50 mL of 10 wt % sodium carbonate aqueous solution was added and after that, the reaction solution was stirred at room temperature for 30 minutes. Then, 1.50 g (1.3 mmol) of tetrakis(triphenylphosphine)palladium was added and after that, the reaction solution was stirred for five hours under reflux. After the reaction ended, crystals which deposited when the reaction solution was cooled were obtained by filtration. Then, these crystals were dissolved in chlorobenzene by heating and after that, the solution was filtered while being hot through a short alumina column to remove residual palladium and the like. Subsequently, this filtrate was concentrated under a reduced pressure and thereby a crude product was obtained. Then the crude product was heated and washed as a slurry with a mixed ethanol/chloroform solvent and after the solution was cooled, crystals obtained by filtration were heat-dried under vacuum and thereby 6.80 g (yield 71%) of halogenated compound X-20 was obtained.

(2) Synthesis of Example Compound A-02

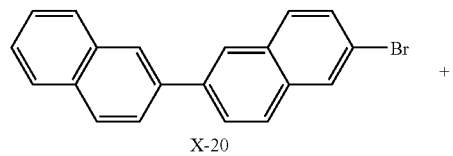

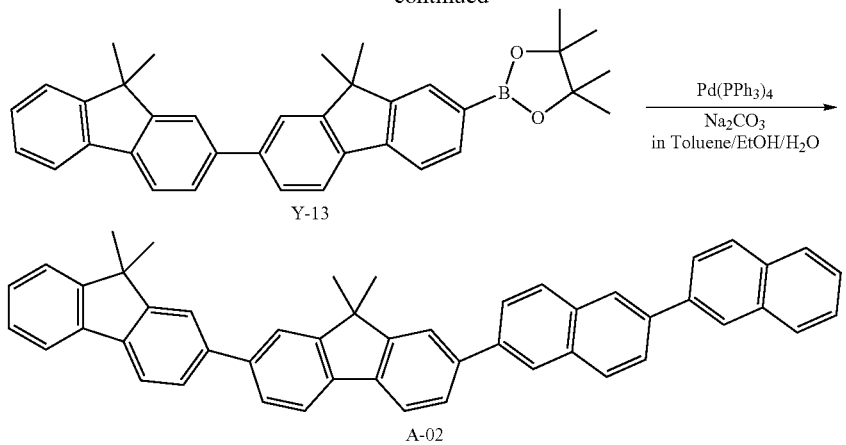

The reagents and the solvent shown below were charged to a 300-mL round-bottomed flask under nitrogen.

Halogenated compound X-20: 2.50 g (7.50 mmol)
Boronate compound Y-13: 4.04 g (7.88 mmol)
Toluene: 100 mL
Ethanol: 50 mL Then, 50 mL of 10 wt % sodium carbonate aqueous solution was added and after that, the reaction solution was stirred at room temperature for 30 minutes. Then, 0.43 g (0.38 mmol) of tetrakis(triphenylphosphine)palladium was added and after that, the reaction solution was stirred for five hours under reflux. After the reaction ended, crystals which deposited when the reaction solution was cooled were obtained by filtration. Then, these crystals were dissolved in chlorobenzene by heating and after that, the solution was filtered while being hot through a short column packed with layered alumina/silica gel to remove residual palladium and the like. Subsequently, this filtrate was concentrated under a reduced pressure and thereby a crude product was obtained. Then the crude product was heated and washed as a slurry with a toluene solvent and after that, recrystallized from chlorobenzene solvent, and crystals obtained by filtration were heat-dried under vacuum at 160° C. and thereby 4.38 g (yield 91%) of Example Compound A-02 was obtained. Sublimation purification was further performed under the conditions of $10^{-4}$ Pa, at 360° C. and thereby 3.88 g (sublimation purification yield 89%) of highly pure sublimation product was obtained.

The results of identification of the obtained compound are shown below.

[MALDI-TOF-MS (matrix-assisted ionization—time-of-flight mass spectrometry)]
Observed value: m/z=638.41; calculated value: $C_{50}H_{38}$=638.30

[$^1$H-NMR (400 MHz, CDCl$_3$)] δ8.22 (dd, 2H), 8.18 (d, 1H), 8.06 (d, 1H), 8.04 (d, 1H), 8.02-7.80 (m, 10H), 7.78 (dd, 2H), 7.73 (dd, 2H), 7.68 (m, 2H), 7.58-7.45 (m, 3H), 7.36 (m, 2H), 1.67 (s, 6H), 1.58 (s, 6H)

The characteristics shown below were also evaluated for Example Compound A-02.

(A) Molecular Orbital Calculation

Molecular orbital calculation was performed under calculation conditions shown below.

(Calculation Condition)

Gaussian03: x86-Linux-G03RevB.05

B3LYP/6-31G* Opt pop=minimal

Figure 7:
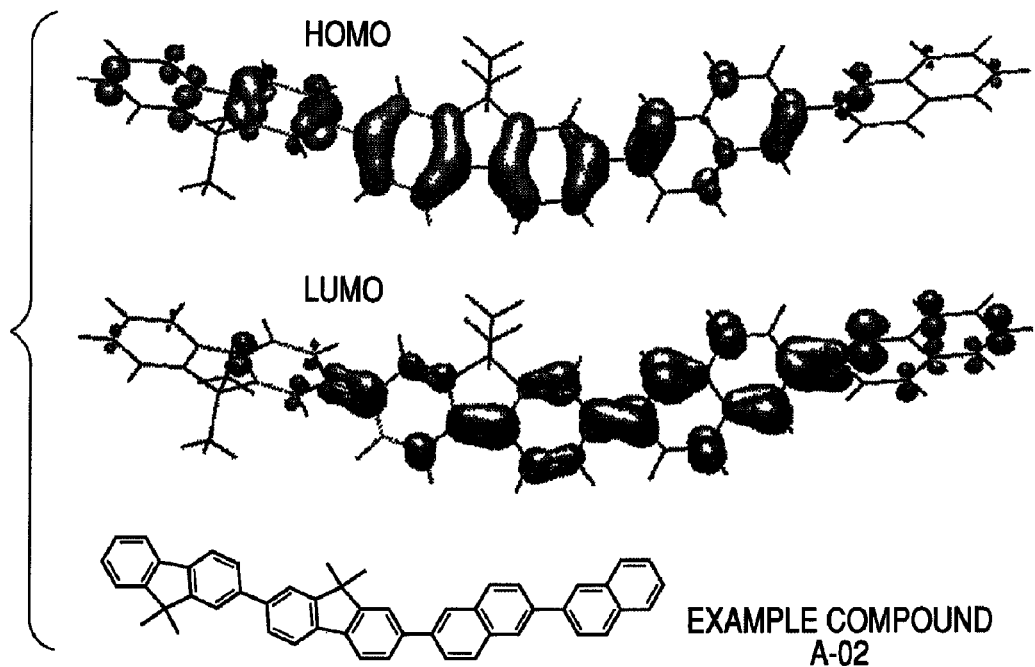
FIG. 7 is a view illustrating molecular orbitals HOMO and LUMO in the results of molecular orbital calculation for Example Compound A-02.

The results of the molecular orbital calculation are described while referring to the drawings. FIG. 7 illustrates molecular orbitals HOMO and LUMO in the results of molecular orbital calculation for Example Compound A-02. As shown in FIG. 7, it was revealed that the HOMO is localized centering at the oligo(fluoren-2,7-diyl) moiety and the LUMO is localized centering at the 2,2'-binaphthyl moiety respectively and that the compound had CT nature. Here, the CT nature means that the HOMO is localized centering at the fluorene moiety whereas the LUMO is localized centering at the naphthalene moiety.

(B) Ionization Potential

Example Compound A-02 was dissolved chloroform to prepare 0.1 wt % chloroform solution. Then, this chloroform solution was dropped onto a glass substrate and a thin film was obtained by spin-coating. Ionization potential was measured by using a photoelectron spectrometer AC-2 (manufactured by Riken Keiki Co., Ltd.) for this thin film. As a result of measurement, the ionization potential of Example Compound A-02 was 5.69 eV.

(C) Solubility

Solubility of Example Compound A-02 in chlorobenzene heated at 130° C. was examined. As a result, the solubility was 16.0 g/L and it was found that the compound showed a high solubility.

(D) Triplet Excitation Level (T$_1$ Level)

At first, Example Compound A-02 and Ir(ppy)$_3$ shown below were dissolved in chloroform to prepare a 0.1 wt % chloroform solution. Here, Ir(ppy)$_3$ is a sensitizer and the weight concentration ratio of Example Compound A-02 to Ir(ppy)$_3$ was 3:1.

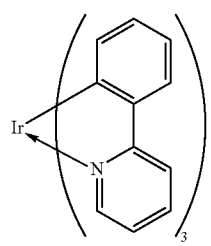

Ir(ppy)$_3$

Then, a thin film was obtained by spin-coating this chloroform solution on a glass substrate. Phosphorescence spectrum was measured for this film under Ar at 77 K and at an excitation wavelength of 350 nm. The triplet excitation level ($T_1$ level) evaluated from the peak wavelength of the first light emission peak of the obtained phosphorescence spectrum was 2.11 eV (corresponding wavelength: 588 nm).

Example 2

Synthesis of Example Compound A-17

(1) Synthesis of Halogenated Compound X-27

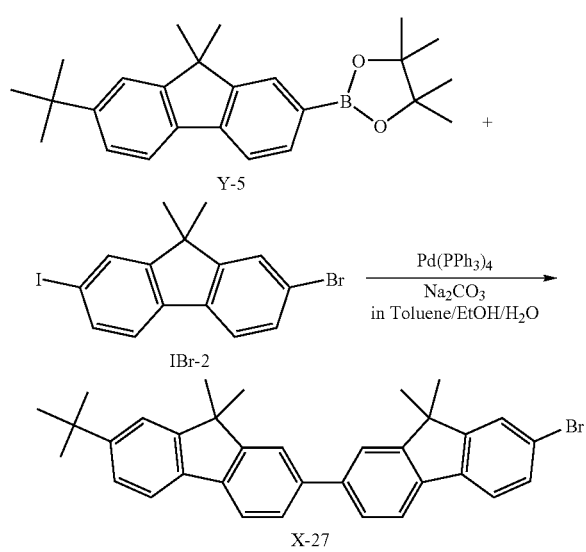

The reagents and the solvent shown below were charged to a 100-mL round-bottomed flask under nitrogen.

Boronate compound Y-5: 1.00 g (2.66 mmol)
Iodobromo compound IBr-2: 1.16 g (2.92 mmol)
Toluene: 30 mL
Ethanol: 15 mL Then, 15 mL of 10 wt % sodium carbonate aqueous solution was added and after that, the reaction solution was stirred at room temperature for 30 minutes. Subsequently, 0.15 g (0.13 mmol) of tetrakis(triphenylphosphine)palladium was added and the reaction solution was stirred and heated at reflux for seven hours. Then, the reaction solution was cooled to room temperature and after that, water was added to quench the reaction. Then, toluene was added and the product contained in the organic layer was extracted by liquid separation operation. Then, this organic layer was washed with pure water twice and after that, dried over sodium sulphate and concentrated under a reduced pressure to obtain a crude product. Subsequently, this crude product was purified by silica gel column chromatography (eluent: heptane/toluene=3/1). Then, 1.15 g of halogenated compound X-27 (yield 83%) was obtained by heating and washing the slurry with a mixed ethanol/heptane solvent.

(2) Synthesis of Boronate Compound Y-12

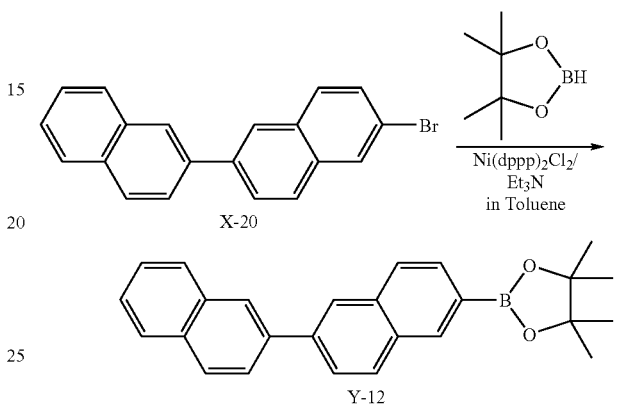

The reagents and the solvent shown below were charged to a 300-mL three-necked flask under nitrogen.

Dehydrated toluene: 120 mL
Halogenated compound X-20: 3.50 g (10.5 mmol) (1,3-bis[diphenylphosphino]propane) dichloronickel(II): 1.14 g (0.75 mmol)

Then, the reagents shown below were added and after that, the reaction solution was stirred for eight hours while heating at 95° C. to 100° C.

Triethylamine: 4.37 mL (31.5 mmol) 4,4,5,5-tetramethyl-1,3,2-dioxabororane: 4.57 mL (31.5 mmol)

Then, the reaction solution was cooled to room temperature and after that, water was added to quench the reaction. Then the reaction solution was filtered to remove insoluble matters. The product in the filtrate was extracted with toluene and this extract was washed with a sodium chloride aqueous solution and, after drying, concentrated under a reduced pressure to obtain a crude product. The obtained crude product was purified by silica gel column chromatography (eluent: heptane/toluene=2/1) and thereby 2.88 g of boronate compound Y-12 (yield 72%) was obtained.

(3) Synthesis of Example Compound A-17

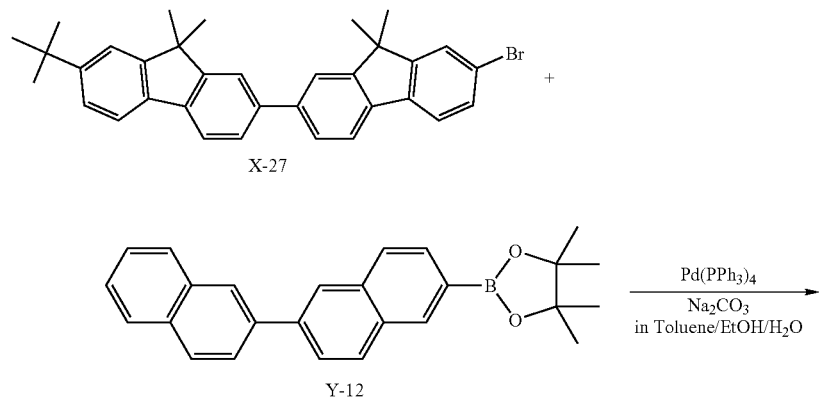

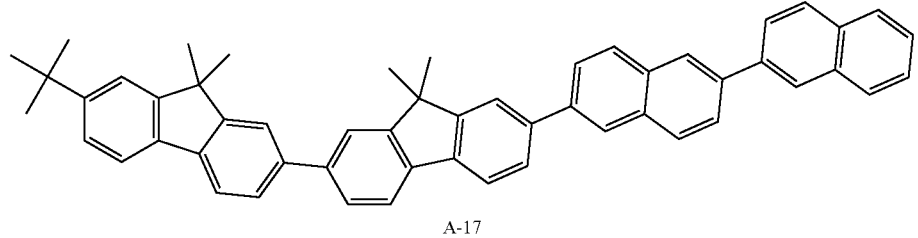

A-17

The reagents and the solvent shown below were charged to a 100-mL round-bottomed flask under nitrogen.

Halogenated compound X-27: 0.60 g (1.16 mmol)
Boronate compound Y-12: 0.40 g (1.05 mmol)
Toluene: 20 mL
Ethanol: 10 mL Then, 10 mL of 10 wt % sodium carbonate aqueous solution was added and after that, the reaction solution was stirred at room temperature for 30 minutes. Subsequently, 60 mg (0.05 mmol) of tetrakis(triphenylphosphine) palladium was added and the reaction solution was stirred and heated at reflux for five hours. Then, the reaction solution was cooled to room temperature and after that, water was added to quench the reaction. Then, the product was extracted with chloroform by liquid separation operation. Then, this extract was washed with pure water twice and after that, dried over sodium sulphate and concentrated under a reduced pressure to obtain a crude product. Subsequently, this crude product was dissolved in chloroform and after that, the solution was filtered while being hot through a short column packed with layered alumina/silica to remove residual palladium and the like. Subsequently, this filtrate was concentrated under a reduced pressure and thereby crude crystals were obtained. Then these crude crystals were heated and washed as a slurry with a heptane/toluene solvent. Subsequently, crystals obtained by recrystallization from a toluene solvent were heat-dried at 160° C. under vacuum and thereby 670 mg (yield 92%) of Example Compound A-17 was obtained. Sublimation purification was further performed under reduced pressure of $10^{-4}$ Pa at 380° C. and thereby 455 mg (sublimation purification yield 68%) of highly pure sublimation product was obtained.

The results of identification of the obtained compound are shown below.

[MALDI-TOF-MS]
Observed value: m/z=694.37; calculated value: $C_{54}H_{46}$=694.36

[$^1$H-NMR (400 MHz, CDCl$_3$)] δ 8.22 (dd, 2H), 8.18 (d, 1H), 8.06 (d, 1H), 8.04 (d, 1H), 8.02-7.83 (m, 9H), 7.82-7.75 (m, 2H), 7.74 (d, 1H), 7.72-7.66 (m, 3H), 7.65 (dd, 1H), 7.53 (m, 2H), 7.48 (d, 1H), 7.41 (dd, 1H), 1.67 (s, 6H), 1.58 (s, 6H), 1.41 (s, 9H)

The characteristics shown below were also evaluated for Example Compound A-17.

(A) Molecular Orbital Calculation

Molecular orbital calculation was performed under the similar conditions as in Example 1. As a result, it was confirmed that Example Compound A-17 had CT nature like Example Compound A-02.

(B) Ionization Potential

Ionization potential was measured under the same conditions as in Example 1. As a result, the ionization potential of Example Compound A-17 was 5.53 eV.

(C) Solubility

Solubility of Example Compound A-17 in chlorobenzene heated at 130° C. was examined. As a result, the solubility was 22.4 g/L and it was found that the compound showed a high solubility.

(D) Triplet Excitation Level (T$_1$ Level)

At first, a thin film was formed on a glass substrate in the same method as in Example 1. Measurement was performed for this film as in Example 1, and the T$_1$ level was evaluated in the same method as in Example 1. The T$_1$ level was 2.13 eV (corresponding wavelength: 582 nm).

Example 3

Synthesis of Example Compound B-18

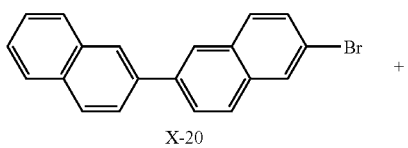

X-20

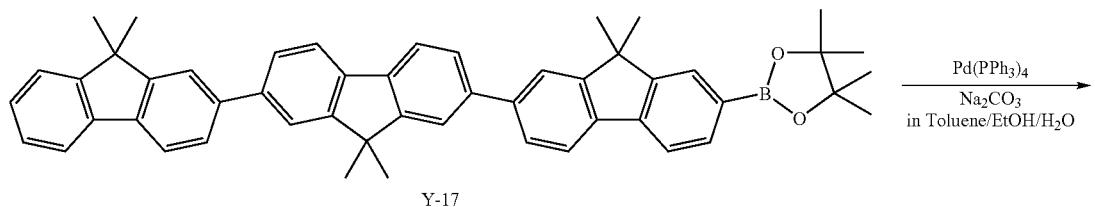

Y-17

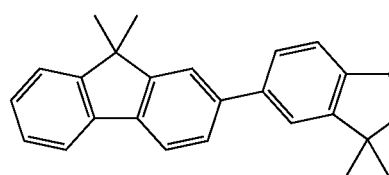

B-18

The reagents and the solvent shown below were charged to a 300-mL round-bottomed flask under nitrogen.

Halogenated compound X-20: 0.68 g (2.04 mmol)
Boronate compound Y-17: 1.30 g (1.84 mmol)
Toluene: 80 mL
Ethanol: 40 mL Then, 40 mL of 10 wt % sodium carbonate aqueous solution was added and after that, the reaction solution was stirred at room temperature for 30 minutes. Subsequently, 0.11 g (0.095 mmol) of tetrakis(triphenylphosphine)palladium was added and the reaction solution was stirred for four hours under reflux. Then, the reaction solution was cooled and, crystals deposited in the reaction solution were then obtained by filtration. Then, the crystals obtained by filtration was heated and dissolved in chlorobenzene, and after that, the solution was filtered while being hot through a small amount of alumina to remove residual palladium and the like. Subsequently, this filtrate was concentrated under a reduced pressure and thereby a crude product was obtained. Then the crude product was recrystallized from chlorobenzene solvent twice. The crystals obtained by filtration were combined and heat-dried at 160° C. under vacuum and thereby 986 mg (yield 64%) of Example Compound B-18 was obtained. Sublimation purification was further performed under reduced pressure of $10^{-4}$ Pa at 420° C. and thereby 531 mg (sublimation purification yield 54%) of highly pure sublimation product was obtained.

The results of identification of the obtained compound are shown below.

[MALDI-TOF-MS]
Observed value: m/z=830.41; Calculated value: $C_{65}H_{50}$=830.39

[$^1$H-NMR (400 MHz, CDCl$_3$)] δ 8.22 (dd, 2H), 8.18 (d, 1H), 8.07 (d, 1H), 8.05 (d, 1H), 8.02-7.80 (m, 12H), 7.80-7.74 (m, 4H), 7.74-7.70 (m, 3H), 7.70-7.65 (m, 3H), 7.53 (m, 2H), 7.47 (dd, 1H), 7.36 (m, 2H), 1.68 (s, 6H), 1.66 (s, 6H), 1.58 (s, 6H)

The characteristics shown below were also evaluated for Example Compound B-18.

(A) Molecular Orbital Calculation

Figure 8:
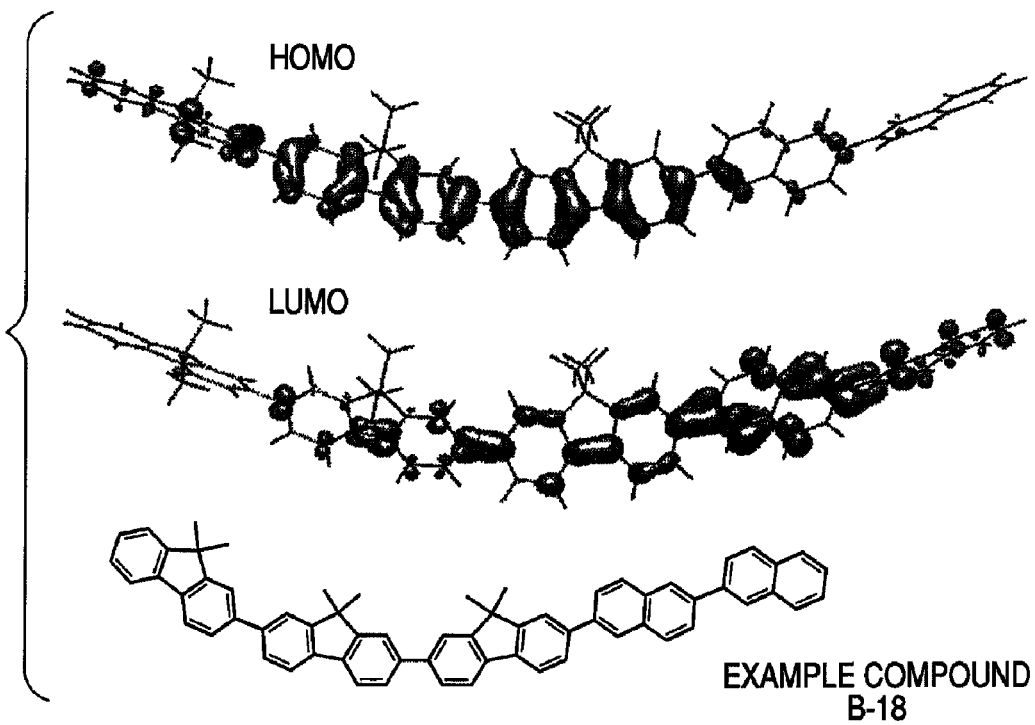
FIG. 8 is a view illustrating molecular orbitals HOMO and LUMO in the results of molecular orbital calculation for Example Compound B-18.

Molecular orbital calculation was performed under the similar conditions as in Example 1. FIG. 8 is a view illustrating molecular orbitals HOMO and LUMO in the results of molecular orbital calculation for Example Compound B-18. As shown in FIG. 8, it was confirmed that Example Compound B-18 had CT nature like Example Compound A-02.

(B) Ionization Potential

Ionization potential was measured under the same conditions as in Example 1. As a result, the ionization potential of Example Compound B-18 was 5.72 eV.

(C) Solubility

Solubility of Example Compound B-18 in chlorobenzene heated at 130° C. was examined. As a result, the solubility was 9.4 g/L and it was found that the compound showed a high solubility.

(D) Triplet Excitation Level (T$_1$ Level)

At first, a thin film was formed on a glass substrate in the same method as in Example 1. Measurement was performed for this film as in Example 1, and the T$_1$ level was evaluated in the same method as in Example 1. The T$_1$ level was 2.14 eV (corresponding wavelength: 579 nm).

Comparative Example 1 to Comparative Example 9

The following characteristics were evaluated for Comparative Compound H-1 (Comparative Example 1) to Comparative Compound H-9 (Comparative Example 9) shown below.

Comparative Compounds

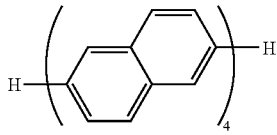

H-1

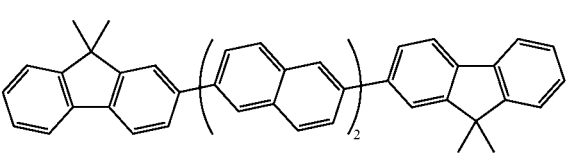

H-2

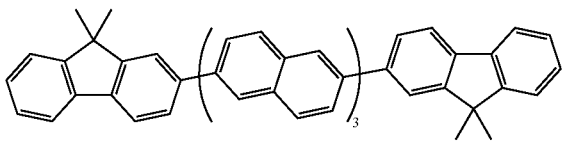

H-3

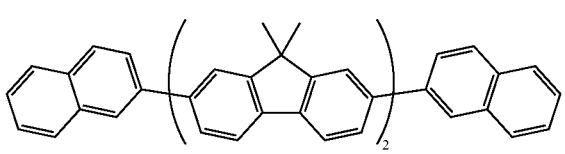

H-4

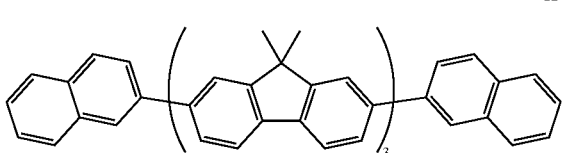

H-5

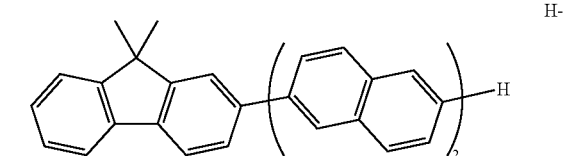

H-6

-continued

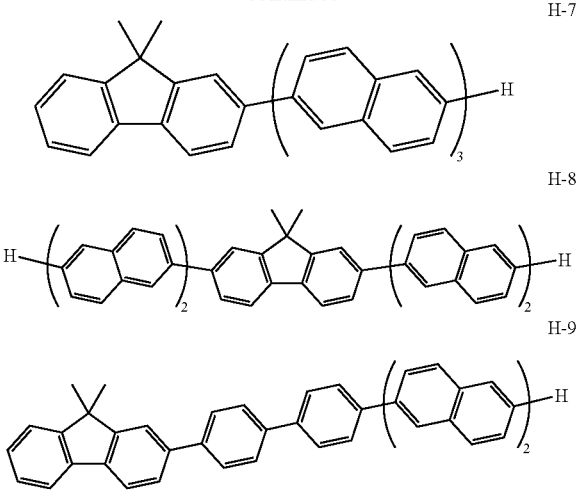

(A) Molecular Orbital Calculation

Figure 9:
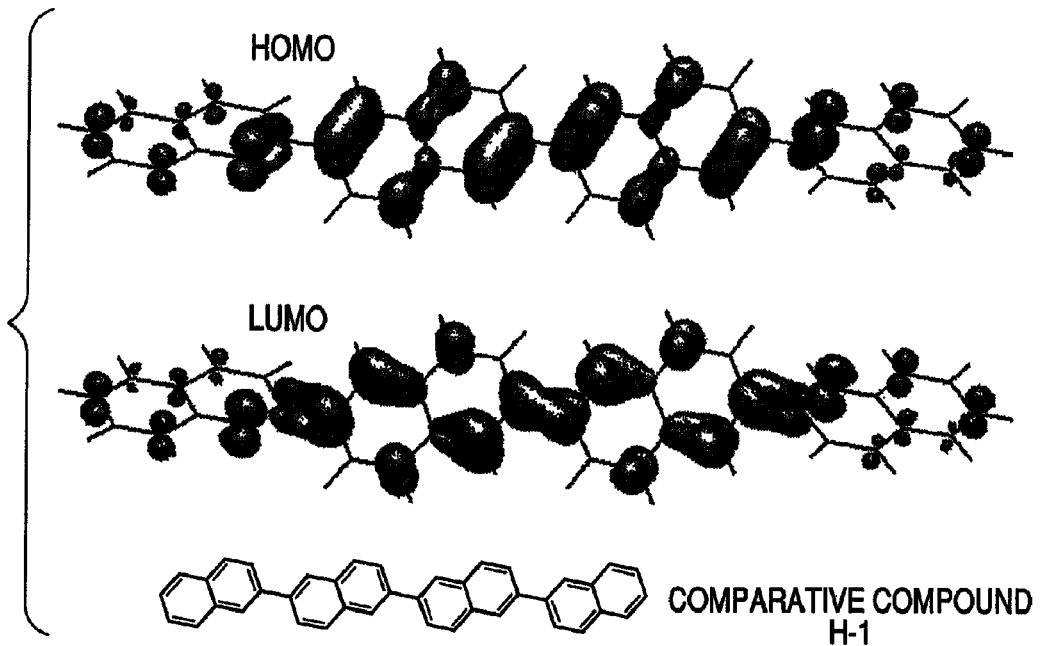
FIG. 9 is a view illustrating molecular orbitals HOMO and LUMO in the results of molecular orbital calculation for Comparative Compound H-1.
Figure 10:
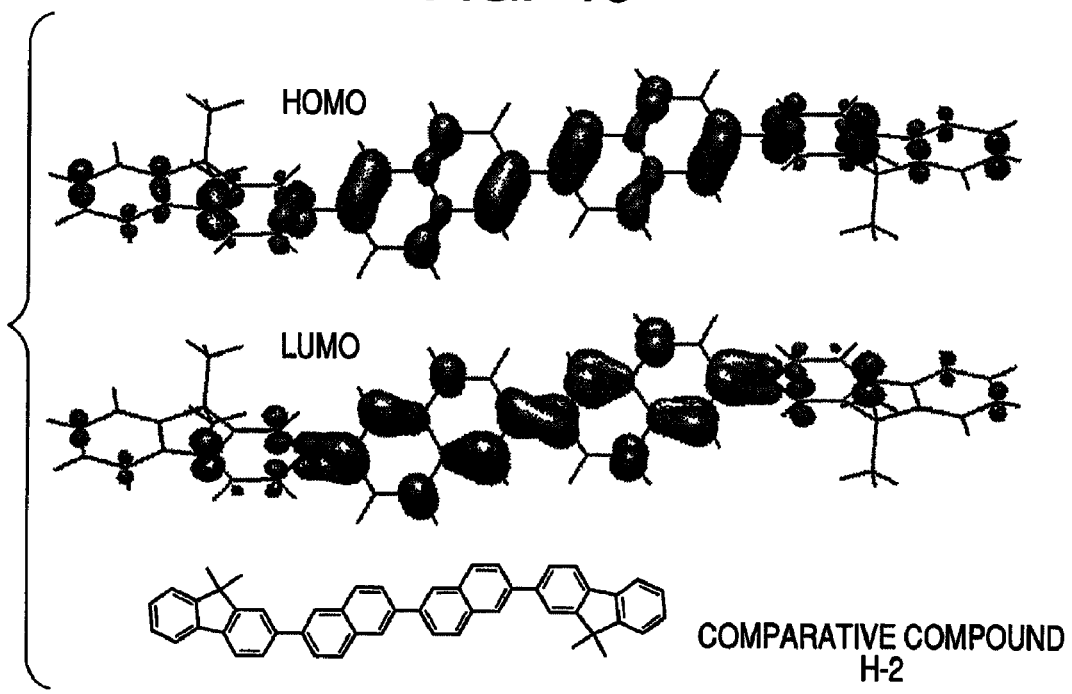
FIG. 10 is a view illustrating molecular orbitals HOMO and LUMO in the results of molecular orbital calculation for Comparative Compound H-2.

Molecular orbital calculation was performed for Comparative Compound H-1 (Comparative Example 1) to Comparative Compound H-9 (Comparative Example 9) under the similar conditions as in Example 1-(A). FIG. 9 is a view illustrating molecular orbitals HOMO and LUMO in the results of molecular orbital calculation for Comparative Compound H-1 (Comparative Example 1). FIG. 10 is a view illustrating molecular orbitals HOMO and LUMO in the results of molecular orbital calculation for Comparative Compound H-2 (Comparative Example 2). As shown in FIGS. 9 and 10, only π-π* nature was recognized in Comparative Compound H-1 and Comparative Compound H-2, and CT nature which was recognized in the binaphthyl compound of the present invention was not recognized. In addition, as a result of molecular orbital calculation for Comparative Compound H-3 (Comparative Example 3) to Comparative Compound H-9 (Comparative Example 9) in the same manner, only π-π* nature was recognized but CT nature which was recognized in the binaphthyl compound of the present invention was not recognized as well.

(B) Comparison in the Ionization Potential

Comparative Compound H-2 (Comparative Example 2), Comparative Compound H-4 (Comparative Example 4) and Comparative Compound H-5 (Comparative Example 5) were respectively synthesized and ionization potential (IP) was measured in the same condition as in Example 1-(B). The results are shown in Table 2 along with those of Examples 1 to 3.

TABLE 2

|  |  | Ionization Potential |
|---|---|---|
| Example 1 | Example Compound A-02 | 5.69 eV |
| Example 2 | Example Compound A-17 | 5.53 eV |
| Example 3 | Example Compound B-18 | 5.72 eV |
| Comparative Example 2 | Comparative Compound H-2 | 5.78 eV |
| Comparative Example 4 | Comparative Compound H-4 | 5.85 eV |
| Comparative Example 5 | Comparative Compound H-5 | 5.83 eV |

(C) Comparison in Solubility

Comparative Compound H-2 (Comparative Example 2), Comparative Compound H-3 (Comparative Example 3) and Comparative Compound H-5 (Comparative Example 5) were respectively synthesized and solubility in chlorobenzene was examined in the same manner as in Example 1-(C). The results are shown in Table 3 along with those of Examples 1 to 3.

TABLE 3

|  |  | Solubility (chlorobenzene, 130° C.) |
|---|---|---|
| Example 1 | Example Compound A-02 | 16.0 g/L |
| Example 2 | Example Compound A-17 | 22.4 g/L |
| Example 3 | Example Compound B-18 | 9.4 g/L |
| Comparative Example 2 | Comparative Compound H-2 | 3.3 g/L |
| Comparative Example 3 | Comparative Compound H-3 | less than 0.6 g/L |
| Comparative Example 5 | Comparative Compound H-5 | 3.5 g/L |

Table 3 revealed that each of the Comparative Compounds is more difficult to dissolve as compared with the binaphthyl compound of the present invention. Here in Table 3, "less than 0.6 g/L" means that 0.6 g of the compound does not completely dissolve in 1 L of chlorobenzene at 130° C.

Example 4

A light emitting element having a structure shown in FIG. 3 was prepared by the following process.

Indium tin oxide (ITO) was film formed as an anode 2 at a film thickness of 120 nm on a glass substrate (substrate 1) by sputtering method and was used as a transparent conductive support substrate (ITO substrate). The following organic compound layers and electrode layers were successively formed on this ITO substrate by vacuum deposition in a vacuum chamber of $10^{-4}$ Pa by resistance heating. Specifically, an α-NPD film was formed in a film thickness 18 nm as a hole transport layer 5 at first. Then, Example Compound A-02 which is a host and Ir(piq)$_3$ which is a guest were co-deposited as a light emitting layer 3 to form a mixture film having a film thickness of 30 nm. Here, the content of Ir(piq)$_3$ for the whole light emitting layer 3 is 10 wt %. Then, a film of Bphen was formed in a film thickness of 40 nm as an electron transport layer 6. Then, a film of KF was formed in a film thickness of 1 nm and then a film of Al was formed in a film thickness of 120 nm. Here, the KF film and the Al film function as a cathode 4.

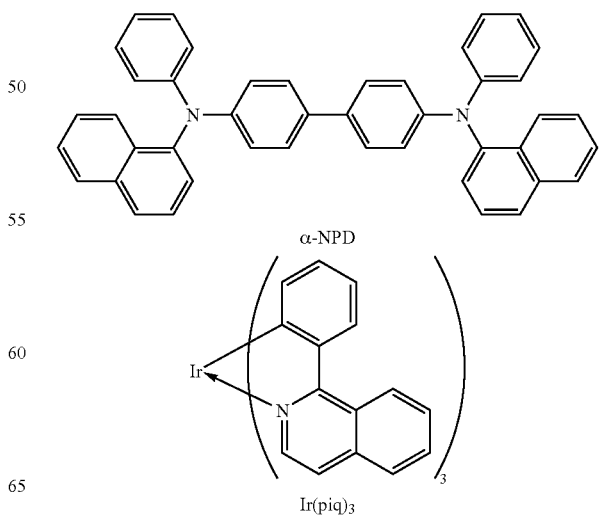

-continued

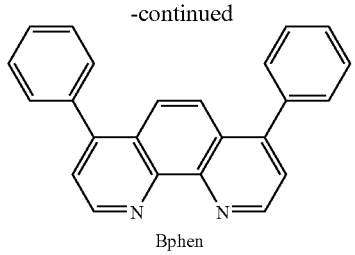

Bphen

Then, a protective glass plate was placed thereon in a dry air atmosphere so as to prevent the organic light emitting element from being deteriorated by the adsorption of moisture and sealed with an acrylic resin adhesive. An organic light emitting element was obtained in this way.

When a voltage of 3.8 V was applied to the obtained organic light emitting element using the ITO electrode (anode 2) as a positive electrode and the Al electrode (cathode 4) as a negative electrode, red light emission having a light emitting efficiency of 6.5 cd/A and a brightness of 800 cd/m$_2$ was observed. The CIE chromaticity coordinates were (x, y)= (0.68, 0.32) in this element. Further, when the element was driven for 200 hours while keeping a constant electric current density of 75 mA/cm$_2$, the ratio of reduction in the brightness from the initial brightness was 10%.

Example 5

An element was prepared in the same process as in Example 4 except that Example Compound A-17 was used in place of Example Compound A-02 as the host of the light emitting layer. The obtained element was evaluated as in Example 4. The results are shown in Table 4.

Example 6

An element was prepared in the same process as in Example 4 except that Example Compound B-18 was used in place of Example Compound A-02 as the host of the light emitting layer. The obtained element was evaluated as in Example 4. The results are shown in Table 4.

Comparative Example 10

An element was prepared in the same process as in Example 4 except that Comparative Compound H-4 was used in place of Example Compound A-02 as the host of the light emitting layer. The obtained element was evaluated as in Example 4. The results are shown in Table 4.

Comparative Example 11

An element was prepared in the same process as in Example 4 except that CBP having a structure shown below was used in place of Example Compound A-02 as the host of the light emitting layer. The obtained element was evaluated as in Example 4. The results are shown in Table 4.

TABLE 4

CBP

|  |  | CIE chromaticity coordinate | Applied voltage @ 800 cd/m$^2$ (V) | Light emitting efficiency @ 800 cd/m$^2$ (cd/A) | Ratio of reduction in brightness after 200 hours @ 75 mA/cm$^2$ |
|---|---|---|---|---|---|
| Example 4 | Example Compound A-02 | (0.68, 0.32) | 3.8 | 6.5 | 10% |
| Example 5 | Example Compound A-17 | (0.68, 0.32) | 4.1 | 5.9 | 16% |
| Example 6 | Example Compound B-18 | (0.68, 0.32) | 3.6 | 6.0 | 12% |
| Comparative Example 10 | Comparative Compound H-4 | (0.67, 0.32) | 5.9 | 4.3 | 55% |
| Comparative Example 11 | CBP | (0.68, 0.32) | 6.0 | 4.9 | 79% |

Example 7

A light emitting element having a structure shown in FIG. 3 was prepared by the following process.

An ITO substrate was prepared by the same process as in Example 4 and the following organic compound layers and electrode layers were successively film formed on this ITO substrate by vacuum deposition in a vacuum chamber of 10$^{-4}$ Pa by resistance heating. Specifically, an α-NPD film was formed in a film thickness of 16 nm as a hole transport layer 5 at first. Then, Example Compound A-02 which is a host and Ir(piq)$_3$ which is a guest and Ir(ppy)$_3$ which is a co-dopant were co-deposited as a light emitting layer 3 to form a mixture film having a film thickness of 50 nm. Here, the content of Ir(piq)$_3$ and Ir(ppy)$_3$ for the whole light emitting layer 3 was 5 wt % and 15 wt %, respectively. Then, a film of Bphen was formed in a film thickness of 50 nm as an electron transport layer 6. Then, a film of KF was formed in a film thickness of 1 nm and then a film of Al was formed in a film thickness of 120 nm. Here, the KF film and the Al film function as a cathode 4.

Then, a protective glass plate was placed thereon in a dry air atmosphere so as to prevent the organic light emitting element from being deteriorated by the adsorption of moisture and sealed with an acrylic resin adhesive. An organic light emitting element was obtained in this way.

When a voltage of 4.0 V was applied to the obtained organic light emitting element using the ITO electrode (anode 2) as a positive electrode and the Al electrode (cathode 4) as a negative electrode, red light emission having a light emitting efficiency of 8.1 cd/A and a brightness of 1000 cd/m$r_2$ was observed. The CIE chromaticity coordinates were (x, y)=(0.68, 0.32) in this element. Further, when the element was driven for 500 hours while keeping a constant electric current density of 100 mA/cm$_2$, the ratio of reduction in the brightness from the initial brightness was 13%.

emitting layer 3 was changed to 25 wt %. The obtained element was evaluated as in Example 7. The results are shown in Table 5.

Comparative Example 12

An element was prepared in the same process as in Example 7 except that Comparative Compound H-2 was used in place of Example Compound A-02 as the host of the light emitting layer. The obtained element was evaluated as in Example 7. The results are shown in Table 5.

Comparative Example 13

An element was prepared in the same process as in Example 7 except that CBP was used in place of Example Compound A-02 as the host of the light emitting layer. The obtained element was evaluated as in Example 7. The results are shown in Table 5.

TABLE 5

| | Host | Co-dopant | CIE chromaticity coordinate | Applied voltage @1000 cd/m$^2$ (V) | Light emitting efficiency @1000 cd/m$^2$ (cd/A) | Ratio of reduction in brightness after 500 hours @100 mA/cm$^2$ |
|---|---|---|---|---|---|---|
| Example 7 | Example Compound A-02 | Ir(ppy)$_3$ | (0.68, 0.32) | 4.0 | 8.1 | 13% |
| Example 8 | Example Compound A-17 | Ir(ppy)$_3$ | (0.68, 0.32) | 4.3 | 7.8 | 21% |
| Example 9 | Example Compound B-18 | Ir(ppy)$_3$ | (0.68, 0.32) | 3.9 | 8.2 | 20% |
| Example 10 | Example Compound A-02 | α-NPD | (0.67, 0.32) | 3.5 | 7.7 | 25% |
| Comparative Example 12 | Comparative Compound H-2 | Ir(ppy)$_3$ | (0.68, 0.32) | 5.2 | 4.3 | 81% |
| Comparative Example 13 | CBP | Ir(ppy)$_3$ | (0.68, 0.32) | 4.6 | 5.6 | 74% |

Example 8

An element was prepared in the same process as in Example 7 except that Example Compound A-17 was used in place of Example Compound A-02 as the host of the light emitting layer. The obtained element was evaluated as in Example 7. The results are shown in Table 5.

Example 9

An element was prepared in the same process as in Example 7 except that Example Compound B-18 was used in place of Example Compound A-02 as the host of the light emitting layer. The obtained element was evaluated as in Example 7. The results are shown in Table 5.

Example 10

An element was prepared in the same process as in Example 7 except that α-NPD was used in place of Ir(ppy)$_3$ as a co-dopant and the content of α-NPD for the whole light

Example 11

A light emitting element having a structure shown in FIG. 3 was prepared by the following process.

An ITO substrate was prepared by the same process as in Example 4 and the following organic compound layers and electrode layers were successively film formed on this ITO substrate by vacuum deposition in a vacuum chamber of 10$^{-4}$ Pa by resistance heating. Specifically, an α-NPD film was formed in a film thickness of 16 nm as a hole transport layer 5 at first. Then, Example Compound B-18 which is a host and BD-1 shown below which is a guest were co-deposited as a light emitting layer 3 to form a mixture film having a film thickness of 30 nm. Here, the content of BD-1 for the whole light emitting layer 3 was 5 wt %. Then, a film of BCP was formed in a film thickness of 30 nm as an electron transport layer 6. Then, a film of KF was formed in a film thickness of 1 nm and then a film of Al was formed in a film thickness of 120 nm. Here, the KF film and the Al film function as a cathode 4.

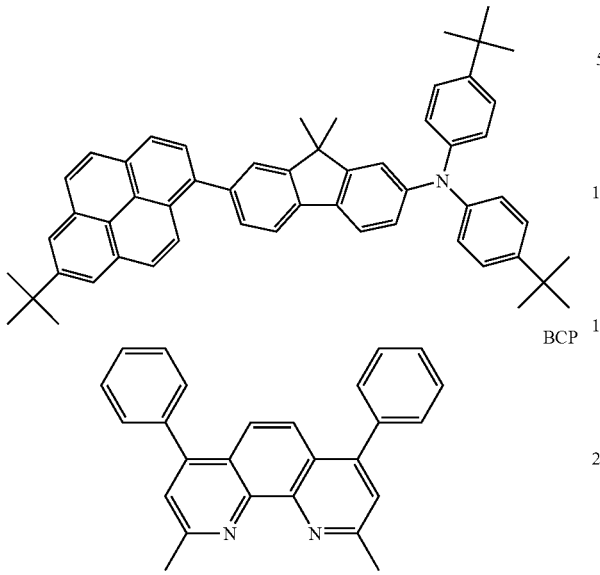

Then, a protective glass plate was placed thereon in a dry air atmosphere so as to prevent the organic light emitting element from being deteriorated by the adsorption of moisture and sealed with an acrylic resin adhesive. An organic light emitting element was obtained in this way.

When a voltage of 5.2 V was applied to the obtained organic light emitting element using the ITO electrode (anode 2) as a positive electrode and the Al electrode (cathode 4) as a negative electrode, blue light emission having a light emitting efficiency of 6.8 cd/A was observed. The CIE chromaticity coordinates were (x, y)=(0.15, 0.14) in this element. Further, when the element was driven for 100 hours while keeping a constant electric current density of 30 mA/cm$_2$, the ratio of reduction in the brightness from the initial brightness was 23%.

Example 12

A light emitting element having a structure shown in FIG. 3 was prepared by the following procedure.

An ITO substrate was prepared by the same process as in Example 4 and PEDOT (for organic electroluminescence) produced by Bayer AG was dropped onto this ITO substrate and spin-coated for 20 seconds at 1000 rpm. Then the film was dried in a vacuum chamber at 120° C. for one hour and thereby a hole transport layer 5 having a film thickness of 40 nm was formed. Then, a solution prepared according to the following composition was dropped onto the hole transport layer 5 under nitrogen atmosphere and spin-coated for 20 seconds at 2000 rpm.

Dehydrated chloroform: 10 g
Example Compound C-18:100 mg
Ir(tBupiq)$_3$ shown below: 9 mg

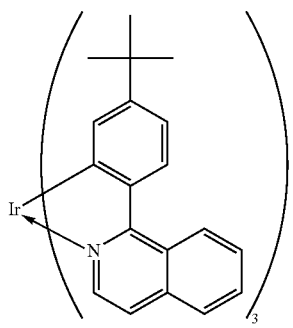

Then, the light emitting layer 3 having a film thickness of 50 nm was formed by drying the film in a vacuum chamber at 120° C. for one hour.

Then, the substrate on which the layers to the light emitting layer 3 were laminated was mounted in a vacuum deposition chamber. Then, Bphen was deposited to form a thin film having a film thickness of 40 nm as an electron transport layer 6. The total film thickness of the organic compound layer is 130 nm up to this step. Then, a film of KF was formed in a film thickness of 1 nm by vacuum deposition and then a film of Al was formed in a film thickness of 120 nm by vacuum deposition. Here, the KF film and the Al film function as a cathode 4. An organic light emitting element was obtained in this way.

Characteristics of the obtained organic light emitting element were evaluated by applying a DC voltage to the element using the ITO electrode (anode 2) as a positive electrode and the Al electrode (cathode 4) as a negative electrode. In this element, current efficiency when the brightness is set to 500 cd/m$_2$ was 1.6 cd/A, and electric power efficiency was 1.8 m/W. The peak in the emission spectrum at this time was 621 nm and the CIE chromaticity coordinates was (x, y)=(0.68, 0.32).

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2007-259866, filed Oct. 3, 2007, which is hereby incorporated by reference herein in its entirety.

What is claimed is:
1. A binaphthyl compound represented by the following general formula [I]:

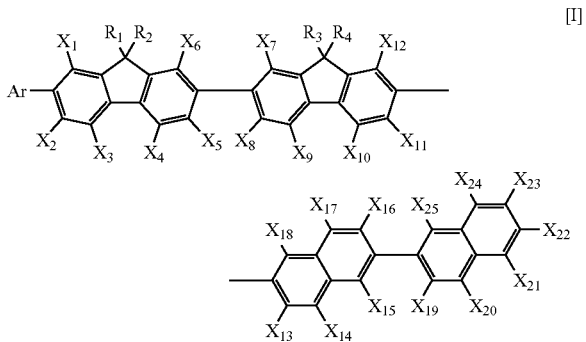

(In Formula (I), Ar represents a hydrogen atom or a substituent group selected from the group consisting of a substituted or unsubstituted alkyl group, a substituted or unsubstituted alkoxy group, a substituted or unsubstituted phenyl group, a substituted or unsubstituted fluorenyl group and a substituted or unsubstituted heteroaromatic ring group;

$X_1$ to $X_{25}$ each represents a hydrogen atom, a substituent group selected from the group consisting of a substituted or unsubstituted alkyl group and a substituted or unsubstituted alkoxy group; and $R_1$ to $R_4$ each represents a hydrogen atom or a substituted or unsubstituted alkyl group).

2. The binaphthyl compound according to claim 1 represented by the following general formula [II]:

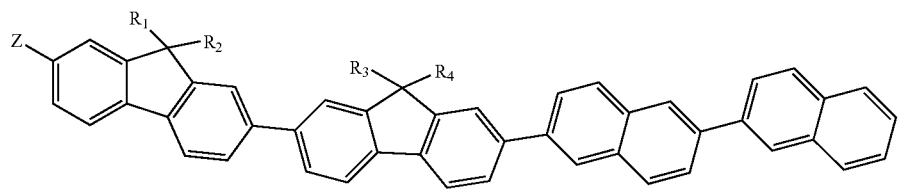

(II)

(In Formula [II], Z represents a hydrogen atom or a substituted or unsubstituted fluorenyl group; and $R_1$ to $R_4$ each represents a hydrogen atom or a substituted or unsubstituted alkyl group).

3. An organic light emitting element comprising an anode and a cathode, and a layer comprising an organic compound sandwiched between the anode and the cathode, wherein one of the anode and the cathode is transparent or semi-transparent, and the layer comprising an organic compound comprises at least one binaphthyl compound according to claim 1.

4. The organic light emitting element according to claim 3, wherein the binaphthyl compound is contained in a light emitting layer.

5. The organic light emitting element according to claim 3, which is an electroluminescent element emitting light by applying a voltage between the anode and the cathode.

6. The organic light emitting element according to claim 4, wherein the light emitting layer comprises a host and a guest and the host is the binaphthyl compound.

7. The organic light emitting element according to claim 6, wherein the guest is a phosphorescence emitting compound.

8. The organic light emitting element according to claim 7, wherein the phosphorescence emitting compound is an iridium complex.

9. The organic light emitting element according to claim 4, wherein the light emitting layer comprises two or more phosphorescence emitting compounds.

10. A display apparatus comprising an organic light emitting element according to claim 3.

* * * * *